US012736475B2

(12) United States Patent
Nishihara et al.

(10) Patent No.: US 12,736,475 B2

(45) Date of Patent: Sep. 15, 2026

(54) LUMINESCENT SUBSTRATE COMPOUND

(71) Applicant: NATIONAL INSTITUTE OF ADVANCED INDUSTRIAL SCIENCE AND TECHNOLOGY, Tokyo (JP)

(72) Inventors: Ryo Nishihara, Ibaraki (JP); Ryoji Kurita, Ibaraki (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 1037 days.

(21) Appl. No.: 17/911,452

(22) PCT Filed: Mar. 17, 2021

(86) PCT No.: PCT/JP2021/010852

§ 371 (c)(1), (2) Date: Sep. 14, 2022

(87) PCT Pub. No.: WO2021/187531

PCT Pub. Date: Sep. 23, 2021

(65) Prior Publication Data

US 2023/0288338 A1 Sep. 14, 2023

(30) Foreign Application Priority Data

Mar. 17, 2020 (JP) ................................ 2020-046137

(51) Int. Cl.

*G01N 21/00* (2006.01)

*C07D 487/04* (2006.01)

(Continued)

(52) U.S. Cl.

CPC ....... *G01N 21/6428* (2013.01); *C07D 487/04* (2013.01); *G01N 33/6803* (2013.01); *G01N 2021/6439* (2013.01)

(58) Field of Classification Search

CPC ................................................. G01N 21/6428

(Continued)

(56) References Cited

U.S. PATENT DOCUMENTS

2015/0011878 A1* 1/2015 Rao ..................... A61B 5/4848 600/431

2018/0273539 A1 9/2018 Suzuki et al.

FOREIGN PATENT DOCUMENTS

JP 5-60697 A 3/1993

JP 2014-503485 A 2/2014

(Continued)

OTHER PUBLICATIONS

Ohmiya et al. (Chemistry Letters, vol. 22, Issue 12, Dec. 1993, pp. 2149-2152 (Year: 1993).*

(Continued)

*Primary Examiner* — Lyle Alexander

*Assistant Examiner* — Emily R. Berkeley

(74) *Attorney, Agent, or Firm* — Birch, Stewart, Kolasch & Birch, LLP

(57) ABSTRACT

The present invention provides a novel compound or the like useful as a luminescent molecule serving as a substrate for a human-derived protein. The compound according to the present invention is a compound represented by the following formula [I], or a salt thereof, or a hydrate or solvate thereof.

(Continued)

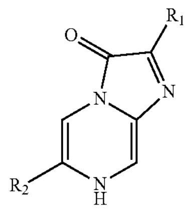

[I]

17 Claims, 6 Drawing Sheets

(51) Int. Cl.
*G01N 21/64* (2006.01)
*G01N 33/68* (2006.01)

(58) Field of Classification Search
USPC ........................................................... 436/86
See application file for complete search history.

(56) References Cited

FOREIGN PATENT DOCUMENTS

| | | | |
|---|---|---|---|
| JP | 2018-158896 | A | 10/2018 |
| JP | 2018-165265 | A | 10/2018 |
| WO | WO 2012/061529 | A1 | 5/2012 |

OTHER PUBLICATIONS

Hirano et al. (Photochem. Photobiol. Sci., 2008, 7, 197-207) (Year: 2008).*

T. Hirano (Japan), Y. Takahashi (Japan), H. Kondo (Japan), H. Ikeda (Japan), S. Maki (Japan), and H. Niwa (Japan) Bioluminescence and Chemiluminescence. Jul. 2007, 11-14 (Year: 2007).*

Kondo et al. Tetrahedron Letters 46 (2005) 7701-7704 (Year: 2005).*

Takahash et al. Tetrahedron Letters 47 (2006) 6057-6061 (Year: 2006).*

Katsunori Teranishi Luminescence 2007; 22: 147â156 (Year: 2007).*

Hirano et al., "Chemiluminescence of Coelenterazine Analogues—Structures of Emitting Species—," Tetrahedron Letters, vol. 33, No. 39, 1992, pp. 5771-5774.

Hollfelder et al., "Characterization of Proton-Transfer Catalysis by Serum Albumins," Journal of the American Chemical Society, vol. 122, 2000, pp. 1022-1029.

International Search Report for International Application No. PCT/JP2021/010852, dated May 11, 2021, with an English translation.

Kubota, "Development of a Simple and Highly Sensitive Measurement System for Antioxidant Potential of Food Ingredients," Technical report of Japan Food Industry Center, No. 27, 2001, pp. 1-20, with an English translation.

Nishihara et al., "Coelenterazine Analogue with Human Serum Albumin-Specific Bioluminescence," Bioconjugate Chemistry, vol. 31, 2020, pp. 2679-2684.

Nishihara et al., "Highly bright and stable NIR-BRET with blue-shifted coelenterazine derivatives for deep-tissue imaging of molecular events in vivo," Theranostics, vol. 9, No. 9, 2019; pp. 2646-2661.

Röthlisberger et al., "Kemp elimination catalysts by computational enzyme design," Nature, vol. 453, 2008, pp. 190-195, 8 pages total.

Vassel et al., "Enzymatic activity of albumin shown by coelenterazine chemiluminescence," Luminescence, vol. 27, 2012, pp. 234-241.

Written Opinion of the International Searching Authority for International Application No. PCT/JP2021/010852, dated May 11, 2021, with an English translation.

Yang et al., "Smart chemiluminescence probes and dual-amplification of signal for detection of amyloid beta species in Alzheimer's disease model," ChemRxiv [online], Apr. 17, 2020, URL: https://chemrxiv.org/articles/preprint/Smart_Chemiluminescence_Probes_and_Dual-Amplification_of_Signal_for_Detection_of_Amyloid_B.

Hirano et al., "The reaction mechanism for the high quantum yield of *Cypridina* (*Vargula*) bioluminescence supported by the chemiluminescence of 6-aryl-2-methylimidazo[1,2-α]pyrazin-3(7H)-ones (*Cypridina* luciferin analogues)," Photochemical & Photobiological Sciences, vol. 7, 2008, pp. 197-207.

Japanese Office Action for Japanese Application No. 2022-508414, dated Jan. 7, 2025, with an English translation.

STN Registry File, RN: 747407-37-0, [online], entered STN on Sep. 19, 2004 (retrieved on Dec. 10, 2024), 1 page total.

STN Registry File, RN: 767284-57-1, [online], entered STN on Oct. 22, 2004 (retrieved on Dec. 10, 2024), 1 page total.

Japanese Office Action for Japanese Application No. 2022-508414, dated Jul. 22, 2025, with English translation.

* cited by examiner

LUMINESCENT SUBSTRATE COMPOUND

TECHNICAL FIELD

The present invention relates to a compound serving as a luminescent substrate, and the use thereof.

BACKGROUND ART

In protein analysis technology, many different types of detection techniques have been conventionally known depending on the intended purpose, including UV absorptiometry based on UV absorption characteristics at 280 nm, and BCA assay designed to use copper reduction for protein detection. However, these techniques are adversely affected by the presence of other biomolecules such as nucleic acids and phospholipids. Moreover, fluorescence-based protein analysis achieves relatively high sensitivity, but the excitation light source used for observation induces high background signals. Thus, current protein analysis technologies not only requires complicated operations such as sample pre-treatment, but are also inefficient in terms of time. In particular, fluorescence-based analysis is unsuitable for continuous observation of in vivo protein kinetics, because the excitation light source used therein may cause protein denaturation and phototoxicity. In addition, fluorometric and absorptiometric reagents that exhibit protein-specific reactions are not easy to develop. Thus, there have been no well-established techniques for simple and highly sensitive quantitative analysis of proteins in solutions of various composition.

On the other hand, a human-derived protein, human serum albumin (HSA), has been widely recognized as an important serum protein responsible for the maintenance of blood osmotic pressure and the transport of endogenous ligands such as bilirubin, and also serves as a catalytic enzyme in the Kemp elimination reaction (i.e., a chemical reaction for proton abstraction from carbon), so that HSA is an important protein which is multi-functional in vivo (e.g., Non-patent Documents 1 and 2).

PRIOR ART DOCUMENTS

Patent Documents

Patent Document 1: JP 2018-158896 A

Patent Document 2: JP 2018-165265 A

Non-Patent Documents

Non-patent Document 1: F. Hollfeider et al., J. Am. Chem, Soc., 2000, 122, 1022-1029.

Non-patent Document 2: D. Rothlisberger et al., Nature, 2008, 453, 190-195.

Non-patent Document 3: T. Hirano et al., Tetrahedron Letters, 1992, 33, 5771-5774.

Non-patent Document 4: R. Nishihara et al., Theranostics, 2019, 9, 2646-2661.

SUMMARY OF THE INVENTION

Problem to be Solved by the Invention

Under these circumstances, there has been a demand for the development of protein analysis technology, e.g., allowing simple and highly sensitive quantitative analysis of a desired protein in solutions of various composition, more specifically the development of a novel luminescent substrate compound which produces light through enzymatic reaction with a human-derived protein.

Means to Solve the Problem

The present invention has been made in consideration of the above situation, and aims to provide compounds and others shown below.

(1) A compound represented by the following formula [I], or a salt thereof, or a hydrate or solvate thereof:

[Formula 1]

[I]

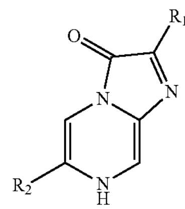

[in formula [I], $R_1$ is —$CH_2$-A (where A is a hydrogen atom or a group represented by the following formula:

[Formula 2]

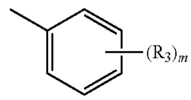

(wherein $R_3$ is a hydrogen atom, a hydroxyl group, a fluorine atom, an alkyl group containing 1 to 5 carbon atoms, a methoxy group, or a trifluoromethyl group, and m is an integer of 0 to 5), or a group represented by the following formula:

[Formula 3]

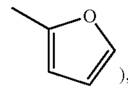

), and $R_2$ is a group represented by the following formula:

[Formula 4]

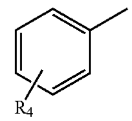

(wherein $R_4$ is (i) —O—$(CH_2)_n$—$R_6$ (where $R_6$ is a hydroxyl group, a methoxy group, a methyl group, a trifluoromethyl group or an azido group, and n is an integer of 1 to 5), (ii) an alkyl group containing 1 to 5 carbon atoms, or (iii) any one of the groups represented by the following formulae:

[Formula 5]

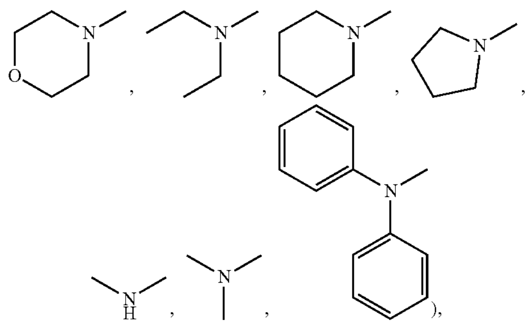

), or a group represented by the following formula:

[Formula 6]

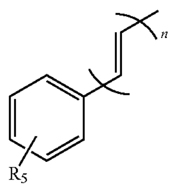

(wherein $R_5$ is (i) a hydrogen atom, a hydroxyl group, a methoxy group, a methyl group, a trifluoromethyl group, a dimethylamino group, a phenyl group, or an azido group, (ii) an alkyl group containing 1 to 5 carbon atoms, (iii) $-O-(CH_2)_p-R_7$ (where $R_7$ is a hydroxyl group, a methoxy group, a methyl group, a trifluoromethyl group, a dimethylamino group, an azido group, or an alkyl group containing 1 to 5 carbon atoms, and p is an integer of 1 to 5), or (iv) any one of the groups represented by the following formulae:

[Formula 7]

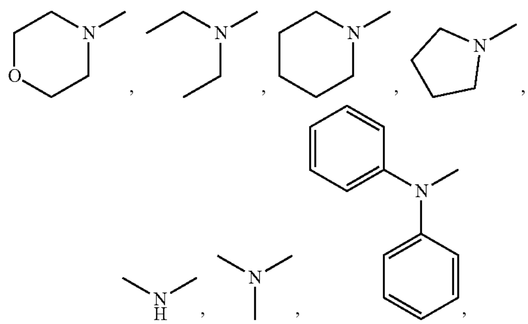

and n is an integer of 0 to 5)].

(2) The compound according to (1) above, or a salt thereof, or a hydrate or solvate thereof, wherein the compound represented by formula [I] is a compound represented by the following formula [II]:

[Formula 8]

(II)

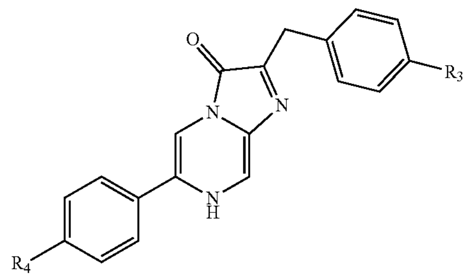

[in formula [II], $R_3$ is a hydrogen atom, a hydroxyl group, a fluorine atom, an alkyl group containing 1 to 5 carbon atoms, a methoxy group, or a trifluoromethyl group, and $R_4$ is (i) $-O-(CH_2)_n-R_6$ (where $R_6$ is a hydroxyl group, a methoxy group, a methyl group, a trifluoromethyl group or an azido group, and n is an integer of 1 to 5), (ii) an alkyl group containing 1 to 5 carbon atoms, or (iii) a group represented by any one of the following formulae:

[Formula 9]

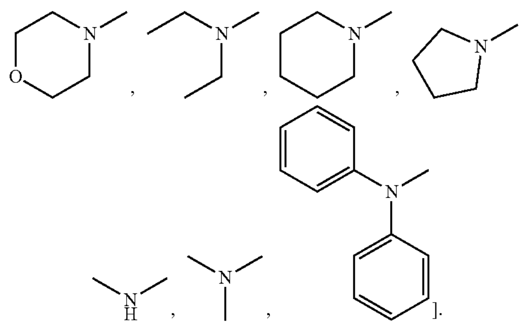

].

(3) The compound according to (1) or (2) above, or a salt thereof, or a hydrate or solvate thereof, wherein $R_3$ and $R_4$ in formula [I] or formula [II] are, in combination, selected from the combinations of groups or atoms indicated in the table below.

TABLE 1

| $R_3$ | $R_4$ |
|---|---|
| —OH | $-O-(CH_2)_2-OH$ |
| —OH | $-O-(CH_2)_3-OH$ |
| —OH | $-O-(CH_2)_4-OH$ |
| —OH | $-O-(CH_2)_5-OH$ |
| —OH | $-O-(CH_2)_3-OCH_3$ |
| —OH | $-O-(CH_2)_2-N_3$ |
| —OH | $-O-(CH_2)_3-CH_3$ |
| —H | $-O-(CH_2)_2-OH$ |
| —H | $-O-(CH_2)_3-OH$ |
| —H | $-O-(CH_2)_4-OH$ |
| —H | $-O-(CH_2)_5-OH$ |
| —H | $-O-(CH_2)_3-OCH_3$ |
| —H | $-O-(CH_2)_3-CH_3$ |
| —OH | $-C_2H_5$ |
| —H | $-C_2H_5$ |
| —OH | $-CH_3$ |
| —H | $-CH_3$ |

(4) The compound according to (3) above, or a salt thereof, or a hydrate or solvate thereof, wherein $R_3$ is —H, and $R_4$ is —O—$(CH_2)_3$—$OCH_3$.

(5) The compound according to (3) above, or a salt thereof, or a hydrate or solvate thereof, wherein $R_3$ is —OH, and $R_4$ is —O—$(CH_2)_3$—$OCH_3$.

(6) The compound according to (1) above, or a salt thereof, or a hydrate or solvate thereof, wherein the compound represented by formula [I] is a compound represented by the following formula [III]:

[Formula 10]

[III]

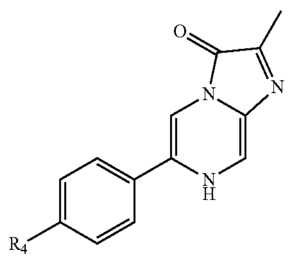

[in formula [III], $R_4$ is (i) —O—$(CH_2)_n$—$R_6$ (where $R_6$ is a hydroxyl group, a methoxy group, a methyl group, a trifluoromethyl group or an azido group, and n is an integer of 1 to 5), (ii) an alkyl group containing 1 to 5 carbon atoms, or (iii) a group represented by any one of the following formulae:

[Formula 11]

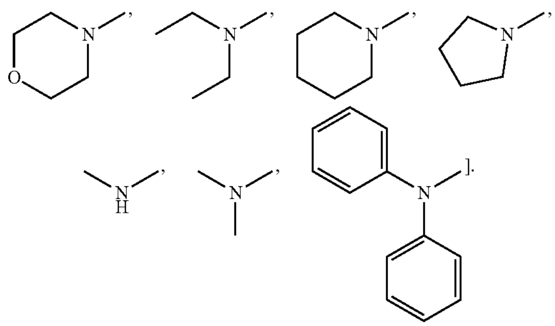

(7) The compound according to (6) above, or a salt thereof, or a hydrate or solvate thereof, wherein $R_4$ in formula [III] is selected from the groups indicated in the table below.

TABLE 2

| $R_4$ |
|---|
| —O—$(CH_2)_2$—OH |
| —O—$(CH_2)_3$—OH |
| —O—$(CH_2)_4$—OH |
| —O—$(CH_2)_5$—OH |
| —O—$(CH_2)_3$—$OCH_3$ |
| —O—$(CH_2)_2$—$N_3$ |
| —O—$(CH_2)_3$—$CH_3$ |

TABLE 2-continued

| $R_4$ |
|---|
| —$C_2H_5$ |
| —$CH_3$ |

(8) The compound according to (7) above, or a salt thereof, or a hydrate or solvate thereof, wherein $R_4$ is —O—$(CH_2)_3$—$OCH_3$.

(9) The compound according to (1) above, or a salt thereof, or a hydrate or solvate thereof, wherein the compound represented by formula [I] is a compound represented by the following formula [IV]:

[Formula 12]

[IV]

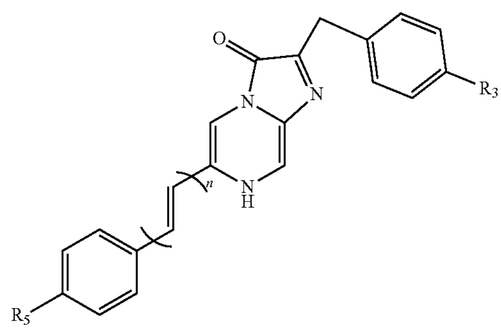

[in formula [IV], $R_3$ is a hydrogen atom, a hydroxyl group, a fluorine atom, an alkyl group containing 1 to 5 carbon atoms, a methoxy group, or a trifluoromethyl group, and $R_5$ is (i) a hydrogen atom, a hydroxyl group, a methoxy group, a methyl group, a trifluoromethyl group, a dimethylamino group, a phenyl group, or an azido group, (ii) an alkyl group containing 1 to 5 carbon atoms, (iii) —O—$(CH_2)_p$—$R_7$ (where $R_7$ is a hydroxyl group, a methoxy group, a methyl group, a trifluoromethyl group, a dimethylamino group, an azido group, or an alkyl group containing 1 to 5 carbon atoms, and p is an integer of 1 to 5), or (iv) any one of the groups represented by the following formulae:

[Formula 13]

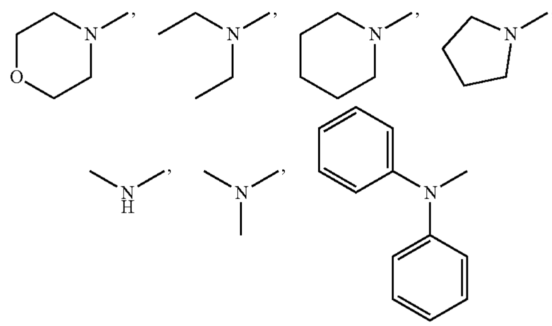

and n is an integer of 0 to 5].

(10) The compound according to (9) above, or a salt thereof, or a hydrate or solvate thereof, wherein n and the groups or atoms represented by $R_3$ and $R_5$ in formula [IV] are, in combination, selected from the combinations indicated in the table below.

TABLE 3

| n | $R_3$ | $R_5$ |
|---|---|---|
| 1 | —OH | —OH |
| 1 | —H | —OH |
| 1 | —OH | —O—$CH_3$ |
| 1 | —H | —O—$CH_3$ |
| 1 | —OH | —$CF_3$ |
| 1 | —H | —$CF_3$ |
| 1 | —H | —N—$(CH_3)_2$ |
| 2 | —H | —O—$CH_3$ |
| 2 | —H | —OH |
| 2 | —H | —$CF_3$ |
| 2 | —H | —N—$(CH_3)_2$ |
| 3 | —H | —O—$CH_3$ |
| 3 | —H | —OH |
| 3 | —H | —$CF_3$ |
| 3 | —H | —N—$(CH_3)_2$ |
| 1 | —H | —O—$(CH_2)_2$—$N_3$ |
| 2 | —H | —O—$(CH_2)_3$—$OCH_3$ |
| 1 | —H | —$C_6H_5$ |
| 1 | —H | —H |

(11) The compound according to (10) above, or a salt thereof, or a hydrate or solvate thereof, wherein n is 1, $R_3$ is —H, and $R_5$ is —$OCH_3$.

(12) The compound according to (10) above, or a salt thereof, or a hydrate or solvate thereof, wherein n is 1, $R_3$ is —H, and $R_5$ is —$CF_3$.

(13) The compound according to (10) above, or a salt thereof, or a hydrate or solvate thereof, wherein n is 1, $R_3$ is —H, and $R_5$ is —$C_6H_5$.

(14) The compound according to (10) above, or a salt thereof, or a hydrate or solvate thereof, wherein n is 1, $R_3$ is —H, and $R_5$ is —H.

(15) A luminescent substrate for proteins or peptides, which comprises the compound according to any one of (1) to (14) above, or a salt thereof, or a hydrate or solvate thereof.

(16) A method for protein or peptide analysis, which comprises administering the compound according to any one of (1) to (14) above, or a salt thereof, or a hydrate or solvate thereof, or the luminescent substrate according to (15) above in vivo or adding the same in vitro to thereby detect a desired protein or peptide.

Effects of the Invention

According to the present invention, a novel compound or the like can be provided as a luminescent molecule serving as a substrate for a human-derived protein (i.e., as a luminescent substrate which produces light through enzymatic reaction with a human-derived protein).

The compound or the like of the present invention has higher luminescence intensity than known luminescent substrate compounds (e.g., coelenterazine derivatives), and is therefore highly useful and practical in the development of protein analysis technology, e.g., allowing simple and highly sensitive quantitative analysis of a desired protein in solutions of various composition.

DESCRIPTION OF EMBODIMENTS

Figure 1:
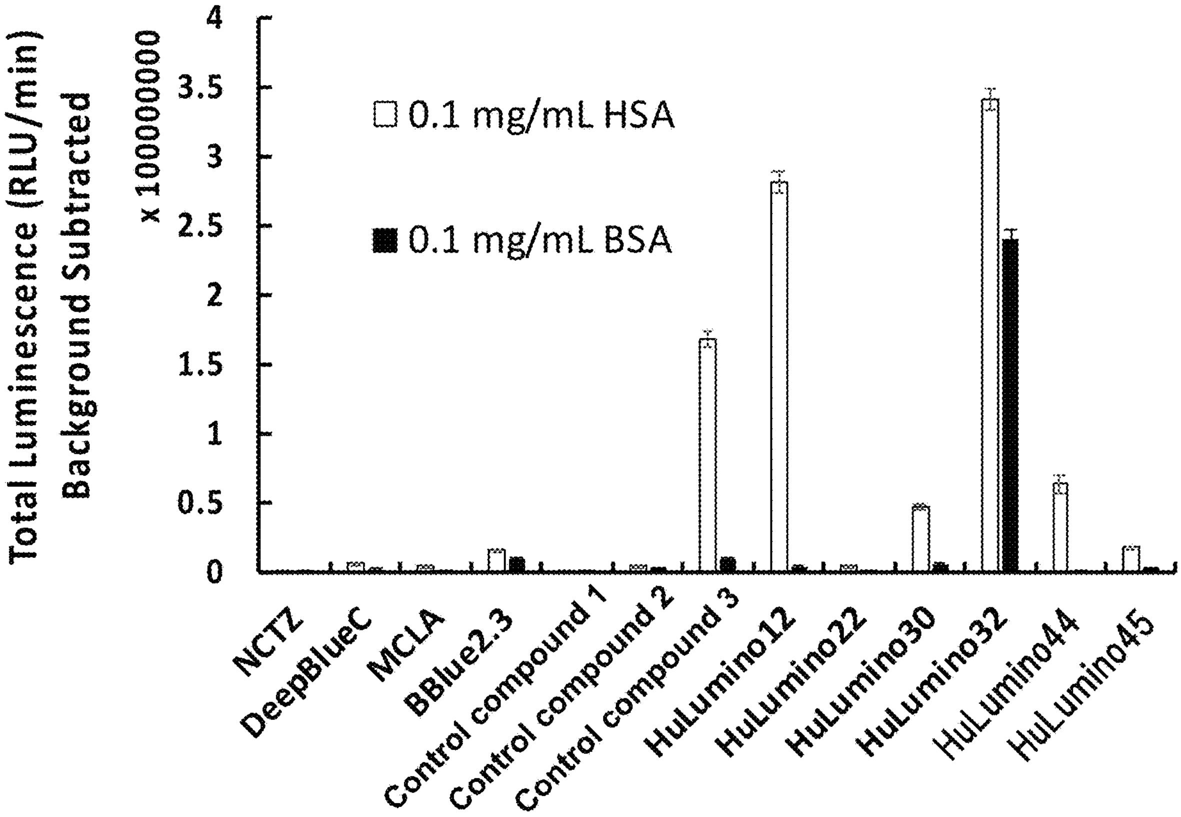
FIG. 1 is a graph showing the luminescence intensity of compounds according to examples of the present invention and comparative examples upon reaction with human or bovine serum albumin.

The present invention will be described in more detail below. The scope of the present invention is not limited by the following description, and any embodiments other than those illustrated below may also be carried out with appropriate modifications without departing from the spirit of the invention.

It should be noted that this specification incorporates the specification of Japanese Patent Application No. 2020-046137 (filed on Mar. 17, 2020) in its entirety, based on which the present application claims priority. Moreover, all publications cited herein, including prior art documents, patent gazettes and other patent documents, are incorporated herein by reference.

1. SUMMARY OF THE PRESENT INVENTION

Luminescent molecules contained in luminous organisms and constituted from amino acids are used as chemical probes for converting molecular recognition or enzymatic reaction into spectral information. Bioanalysis based on such a luminescent reaction allows microanalysis or bioimaging without requiring an excitation light source, and is widely used as a highly sensitive analytical technique in the field of life science. This is attributed to the ability of luminescent molecules to produce excitation energy through chemical reaction. Luminescent systems widely used for bioanalysis include firefly luminescent systems and marine luminous species such as luminous crystal jellyfish. In particular, the *renilla* luciferase (RLuc) luminescent system, which is one of the marine luminous species and uses coelenterazine (CTZ) as a luminescent substrate, is a simple luminescent system that requires no cofactors other than oxygen molecules (in more detail, a simple luminescence mechanism for producing light upon proton transfer in the chemical structure of CTZ), and allows highly reproducible analysis not only within cells but also in an ATP-free extracellular environment. Thus, there have been many reports of CTZ derivatives modified from the chemical structure of CTZ, and their optical properties have been examined in detail (Patent Documents 1 and 2 as well as Non-patent Documents 3 and 4 listed above).

The compound according to the present invention is a compound as a luminescent molecule serving as a substrate for a human-derived protein (i.e., as a luminescent substrate which produces light through enzymatic reaction with a human-derived protein), and has now been found as a compound having higher luminescence intensity than known luminescent substrate compounds as mentioned above and being highly useful and practical.

2. LUMINESCENT SUBSTRATE COMPOUND

The compound according to the present invention (hereinafter also referred to as the compound of the present invention) is a compound represented by the following formula [I].

[Formula 14]

[1]

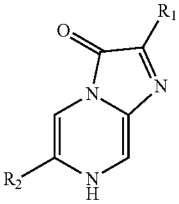

In formula [I], $R_1$ is $—CH_2$-A.

The above A is a hydrogen atom or a group represented by the following formula:

[Formula 15]

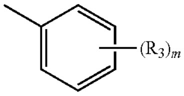

(wherein $R_3$ is a hydrogen atom, a hydroxyl group, a fluorine atom, an alkyl group containing 1 to 5 carbon atoms, a methoxy group, or a trifluoromethyl group, and m is an integer of 0 to 5), or a group represented by the following formula:

[Formula 16]

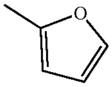

but preferred is the former group.

Moreover, in formula [I], $R_2$ is a group represented by the following formula:

[Formula 17]

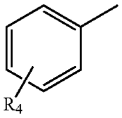

(wherein $R_4$ is (i) $—O—(CH_2)_n—R_6$ (where $R_6$ is a hydroxyl group, a methoxy group, a methyl group, a trifluoromethyl group or an azido group, and n is an integer of 1 to 5), (ii) an alkyl group containing 1 to 5 carbon atoms, or (iii) any one of the groups represented by the following formulae:

[Formula 18]

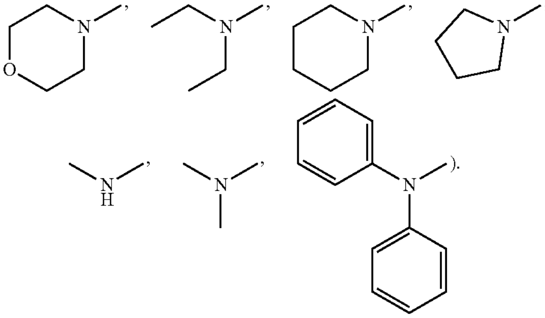

or a group represented by the following formula:

[Formula 19]

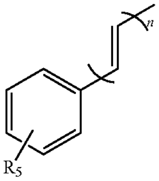

(wherein $R_5$ is (i) a hydrogen atom, a hydroxyl group, a methoxy group, a methyl group, a trifluoromethyl group, a dimethylamino group, a phenyl group, or an azido group, (ii) an alkyl group containing 1 to 5 carbon atoms, (iii) $—O—(CH_2)_p—R_7$ (where $R_7$ is a hydroxyl group, a methoxy group, a methyl group, a trifluoromethyl group, a dimethylamino group, an azido group, or an alkyl group containing 1 to 5 carbon atoms, and p is an integer of 1 to 5), or (iv) any one of the groups represented by the following formulae:

[Formula 20]

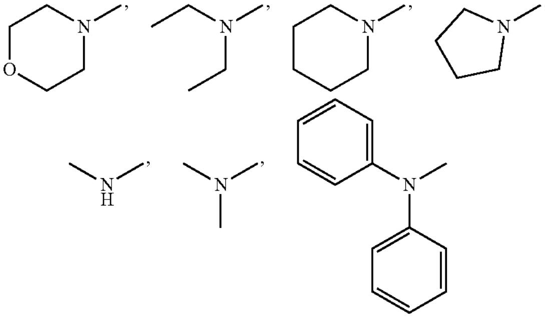

and n is an integer of 0 to 5).

The compound represented by the above formula [I] is preferably exemplified by, but is not limited to, a compound represented by the following formula [II], a compound represented by the following formula [III], and a compound represented by the following formula [IV], etc.

[Formula 21]

[II]

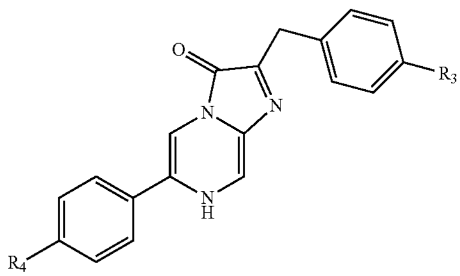

[Formula 22]

[III]

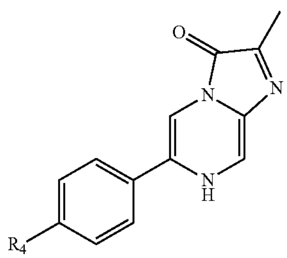

[Formula 23]

[IV]

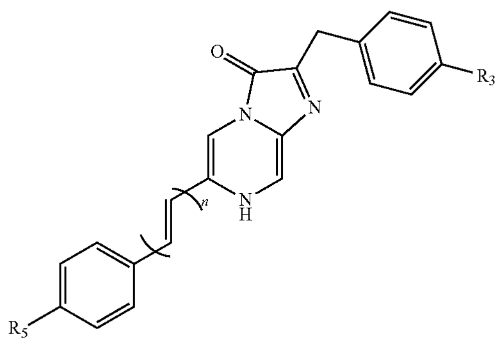

With regard to $R_3$ and $R_4$ in the above formula [II], $R_4$ in the above formula [III], and $R_3$ and $R_5$ as well as n in the above formula [IV], the same explanations as given for $R_3$, $R_4$ and $R_5$ as well as the value of n in the above formula [I] can also be applied.

In the above formula [II], the combination of $R_3$ and $R_4$ is not limited in any way, but preferred examples include those indicated in the table below.

TABLE 4

| Compound name | $R_3$ | $R_4$ |
|---|---|---|
| HuLumino1 | —OH | —O—$(CH_2)_2$—OH |
| HuLumino2 | —OH | —O—$(CH_2)_3$—OH |
| HuLumino3 | —OH | —O—$(CH_2)_4$—OH |
| HuLumino4 | —OH | —O—$(CH_2)_5$—OH |
| HuLumino5 | —OH | —O—$(CH_2)_3$—$OCH_3$ |
| HuLumino6 | —OH | —O—$(CH_2)_2$—$N_3$ |
| HuLumino7 | —OH | —O—$(CH_2)_3$—$CH_3$ |
| HuLumino8 | —H | —O—$(CH_2)_2$—OH |
| HuLumino9 | —H | —O—$(CH_2)_3$—OH |
| HuLumino10 | —H | —O—$(CH2)_4$—OH |
| HuLumino11 | —H | —O—$(CH_2)_5$—OH |
| HuLumino12 | —H | —O—$(CH_2)_3$—$OCH_3$ |
| HuLumino13 | —H | —O—$(CH_2)_3$—$CH_3$ |
| HuLumino14 | —OH | —$C_2H_5$ |
| HuLumino15 | —H | —$C_2H_5$ |
| HuLumino16 | —OH | —$CH_3$ |
| HuLumino17 | —H | —$CH_3$ |

Moreover, specific examples of the compound represented by the above formula [II] also preferably include compounds represented by the following formulae.

[Formula 24]

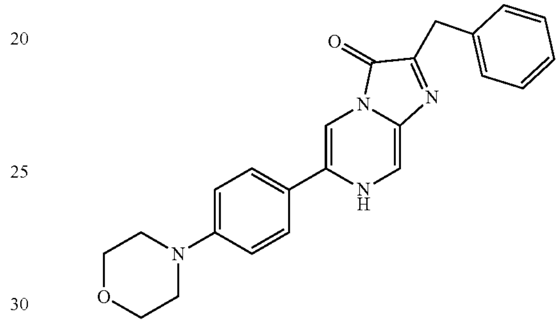

,

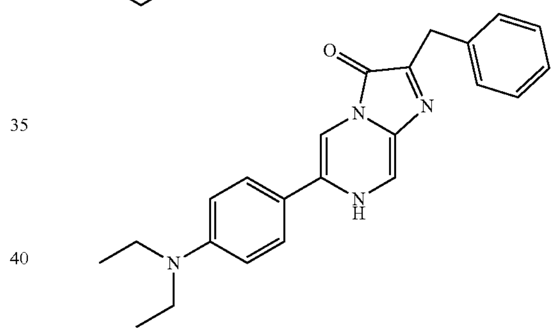

,

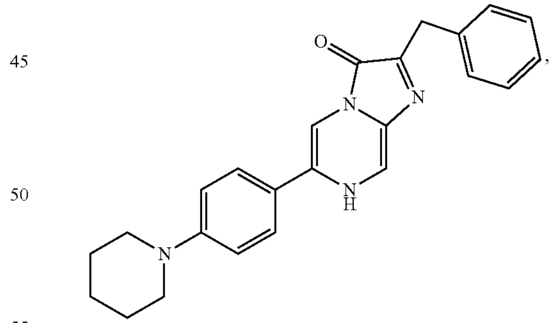

,

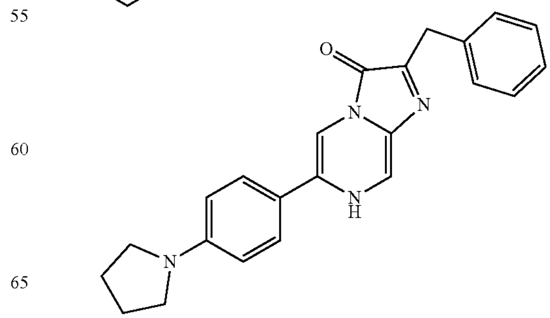

,

-continued

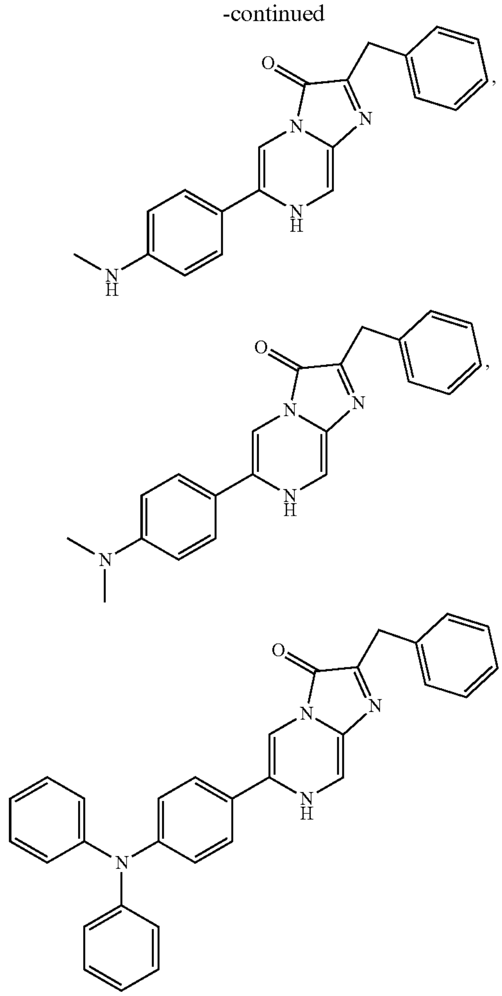

In the above formula [III], $R_4$ is not limited in any way, but preferred examples include those indicated in the table below.

TABLE 5

| Compound name | $R_4$ |
|---|---|
| HuLumino18 | $—O—(CH_2)_2—OH$ |
| HuLumino19 | $—O—(CH_2)_3—OH$ |
| HuLumino20 | $—O—(CH_2)_4—OH$ |
| HuLumino21 | $—O—(CH_2)_5—OH$ |
| HuLumino22 | $—O—(CH_2)_3—OCH_3$ |
| HuLumino23 | $—O—(CH_2)_2—N_3$ |
| HuLumino24 | $—O—(CH_2)_3—CH_3$ |
| HuLumino25 | $—C_2H_5$ |
| HuLumino26 | $—CH_3$ |

In the above formula [IV], the value of n and the combination of $R_3$ and $R_5$ are not limited in any way, but preferred examples include those indicated in the table below.

TABLE 6

| Compound name | n | $R_3$ | $R_5$ |
|---|---|---|---|
| HuLumino27 | 1 | —OH | —OH |
| HuLumino28 | 1 | —H | —OH |
| HuLumino29 | 1 | —OH | $—O—CH_3$ |
| HuLumino30 | 1 | —H | $—O—CH_3$ |
| HuLumino31 | 1 | —OH | $—CF_3$ |
| HuLumino32 | 1 | —H | $—CF_3$ |
| HuLumino33 | 1 | —H | $—N—(CH_3)_2$ |
| HuLumino34 | 2 | —H | $—O—CH_3$ |
| HuLumino35 | 2 | —H | —OH |
| HuLumino36 | 2 | —H | $—CF_3$ |
| HuLumino37 | 2 | —H | $—N—(CH_3)_2$ |
| HuLumino38 | 3 | —H | $—O—CH_3$ |
| HuLumino39 | 3 | —H | —OH |
| HuLumino40 | 3 | —H | $—CF_3$ |
| HuLumino41 | 3 | —H | $—N—(CH_3)_2$ |
| HuLumino42 | 1 | —H | $—O—(CH_2)_2—N_3$ |
| HuLumino43 | 2 | —H | $—O—(CH_2)_3—OCH_3$ |
| HuLumino44 | 1 | —H | $—C_6H_5$ |
| HuLumino45 | 1 | —H | —H |

The compound of the present invention mentioned above may be used in the form of a salt (preferably, e.g., a pharmacologically acceptable salt) in combination with or in place of this compound. Such a salt is not limited in any way, but preferred examples include halogenated hydroacid salts (e.g., hydrochloride salt, hydrobromide salt, and hydroiodide salt), inorganic acid salts (e.g., sulfate salt, nitrate salt, perchlorate salt, phosphate salt, carbonate salt, and bicarbonate salt), organic carboxylic acid salts (e.g., acetate salt, trifluoroacetate salt, maleate salt, tartrate salt, fumarate salt, and citrate salt), organic sulfonic acid salts (e.g., methanesulfonate salt, trifluoromethanesulfonate salt, ethanesulfonate salt, benzenesulfonate salt, toluenesulfonate salt, and camphorsulfonate salt), amino acid salts (e.g., aspartate salt, and glutamate salt), quaternary amine salts, alkali metal salts (e.g., sodium salt, and potassium salt), alkaline earth metal salts (e.g., magnesium salt, and calcium salt), etc.

Moreover, the compound of the present invention encompasses all isomers possible in terms of the compound's structure (e.g., geometrical isomers, optical isomers based on asymmetric carbons, rotational isomers, stereoisomers, and tautomers) and mixtures of two or more of these isomers, and is not limited to the descriptions about the structural formulae shown for convenience' sake. Moreover, the compound of the present invention may be in S-configuration, R-configuration or RS-configuration, and is not limited in any way. Further, the compound of the present invention may be present in the form of a hydrate or solvate, depending on its type. In the present invention, such a hydrate or solvate also falls within the compound of the present invention, and may be used for the same purposes as the compound of the present invention. Such a solvate is not limited in any way, but is exemplified by a solvate with ethanol, etc.

The compound of the present invention (the compound of formula [II]) may be prepared, for example, as shown in reaction scheme 1 below, through condensation between a ketoacetal compound (wherein $R_{3a}$ is a hydroxyl group protected with TBS (t-butyldimethylsilyl) or a hydrogen atom) and a coelenteramine derivative (wherein $R_4$ is as defined above; the same applies hereinafter).

Scheme 1

[Formula 25]

スキーム1

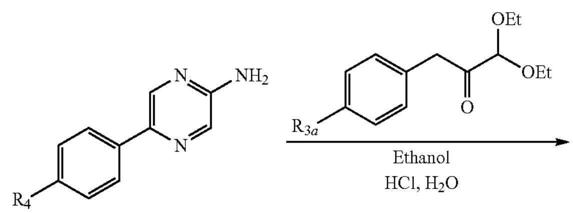

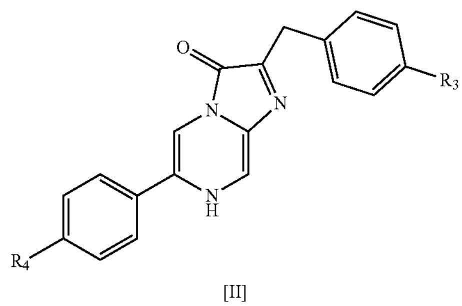

[II]

In the above reaction scheme 1, in the case of preparing a compound in which $R_4$ in the above formula [II] is $—O—(CH_2)_n—R_6$, the coelenteramine derivative used as a starting material in this case may be prepared, for example, according to reaction scheme 2 shown below. It should be noted that in all the reaction schemes shown below, "Boronic acid" is intended to mean the boronic acid derivative shown in each reaction scheme.

Scheme 2

[Formula 26]

スキーム2

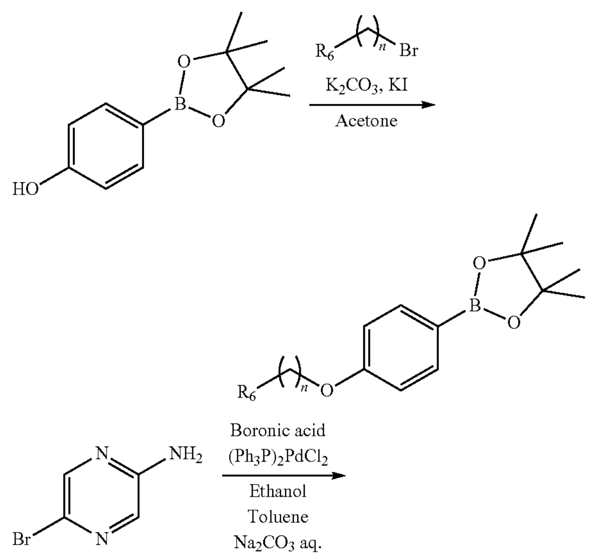

-continued

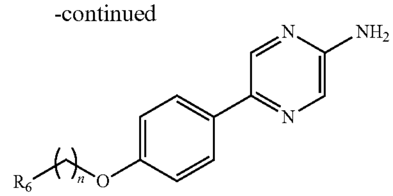

Likewise, in the above reaction scheme 1, in the case of preparing a compound in which $R_4$ in the above formula [II] is an alkyl group containing 1 to 5 carbon atoms, the coelenteramine derivative used as a starting material in this case may be prepared, for example, according to reaction scheme 3 shown below.

Scheme 3

[Formula 27]

スキーム3

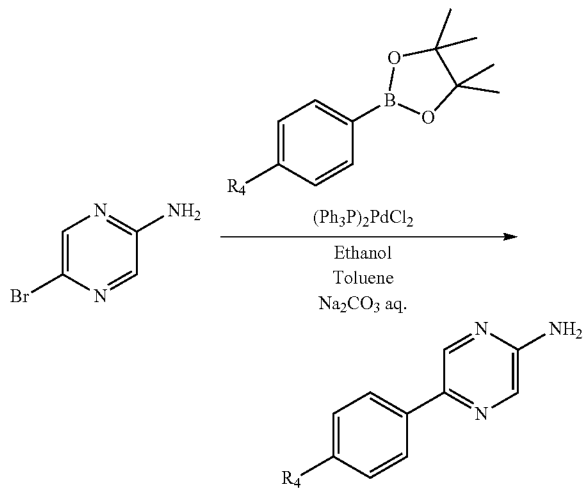

It should be noted that the detailed conditions required for each step in each scheme shown above may be determined as appropriate by those skilled in the art, and in the synthesis examples described later, their respective conditions are given in detail.

The compound of the present invention can be used as a luminescent substrate for a desired protein or peptide. Such a desired protein or peptide is not limited in any way, but is exemplified by those of human origin. Such a desired protein or peptide is not limited in any way, but examples include luciferase enzymes (e.g., *renilla* luciferase (RLuc) luminescent systems RLuc8 (reference document: Loening, A. M. et al., *Protein Eng. Des. Sel.,* 2006, 19, 391-400; Loening, A. M. et al., *J. Mol. Biol.,* 2007, 374, 1017-1028; Loening, A. M. et al., *Protein Eng. Des. Sel.,* 2006, 19, 391-400.) and RLuc8.6 (reference document: Loening, A. M. et al., *Nat. Methods,* 2007, 4, 641-643), and CLuc system (reference document: Mitani, Y. et al., *Protein Expression and Purification,* 2017, 133, 102-109)), as well as human serum albumin (HSA), bovine serum albumin (BSA), etc.

Moreover, the compound of the present invention can also be used in a method for protein or peptide analysis, which comprises administering the compound of the present invention in vivo or adding the same in vitro to thereby detect a desired protein or peptide. Such a protein or peptide is preferably exemplified by those of human origin, and more specifically the same explanation as given above may be applied thereto. The method and conditions for in vivo administration or the method and conditions for in vitro addition are not limited in any way, and may be selected and determined as appropriate while also referring to commonly used well-known methods and conditions. Moreover, the detection of such a protein or peptide is not limited in any way, and any method may be used for this purpose as long as it allows detection of luminescence from the compound of the present invention as a luminescent molecule, and it is possible to use a well-known detection device and/or to determine detection conditions.

The present invention will be further described in more detail by way of the following examples, although the present invention is not limited to these examples.

EXAMPLES

Synthesis Method

The reagents were purchased from Wako Pure Chemical Industries, Ltd., Japan, Kanto Chemical Co., Inc., Japan, Tokyo Kagaku Kenkyusho Co., Ltd., Japan, or Sigma-Aldrich Corporation, and used directly without being purified. In the synthesis of luminescent substrates, silica column chromatography was performed using a silica gel (Merck 1.07734.9025, silica gel 60 (0.063 to 0.200 mm) for column chromatography (70 to 230 mesh ASTM)). $^{1}$H-NMR and $^{13}$C-NMR were performed with a Bruker AvanceIII-500 using tetramethylsilane (TMS, 0 ppm) as an internal standard. The binding constant (J) was expressed in Hz. The abbreviations s, d, t, q, m and br refer to singlet, doublet, triplet, quartet, multiplet and broad, respectively.

Example 1

Synthesis of 2-benzyl-6-(4-(3-methoxypropoxy) phenyl)imidazo[1,2-a]pyrazin-3(7H)-one (HuLumino12)

[Formula 28]

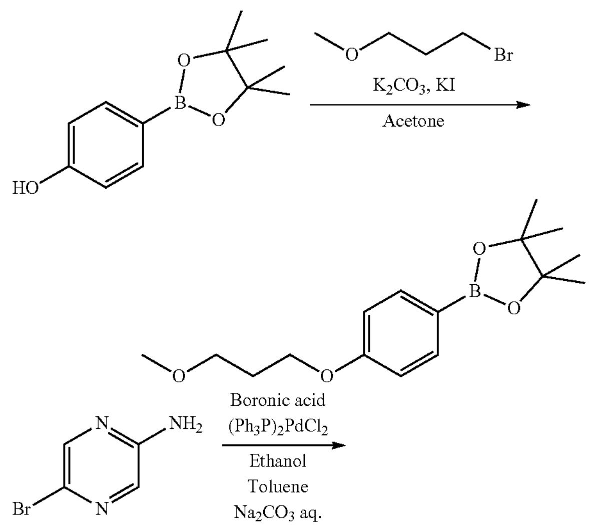

-continued

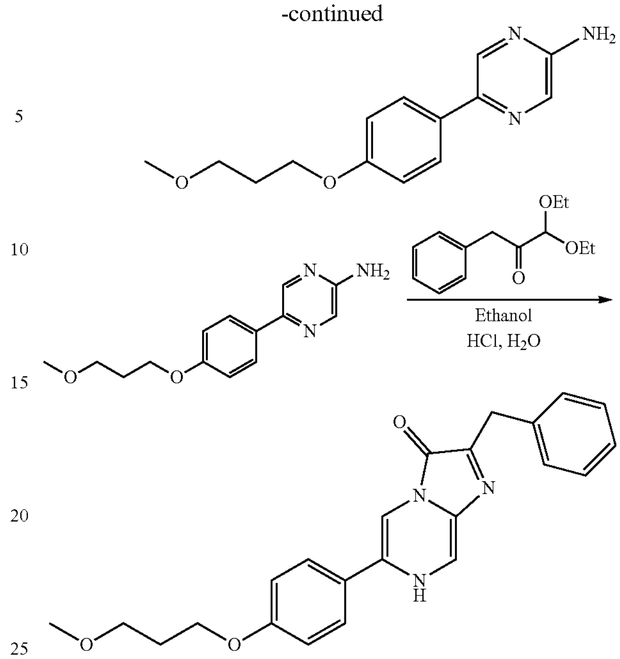

<Synthesis Method>

(1) Under a nitrogen atmosphere, 4-(4,4,5,5-tetramethyl-1,3,2-dioxaborolan-2-yl) phenol (300.0 mg, 1.3 mmol, 1 eq.) and potassium carbonate (246 mg, 1.7 mmol, 1.3 eq.) were dissolved in acetone (20 ml) and stirred at room temperature. To this, a solution of 1-bromo-3-methoxypropane (416.2 mg, 2.7 mmol, 2 eq.) and potassium iodide (12 mg, 0.06 mmol, 0.05 eq.) in acetone (20 ml) was added, followed by stirring overnight (19 hours) at 70° C. After cooling to room temperature, the reaction mixture was concentrated under reduced pressure. The resulting residue was extracted with ethyl acetate, washed with distilled water and saturated aqueous sodium chloride, dried over sodium sulfate, and then concentrated again under reduced pressure. The resulting residue was purified by column chromatography (eluent: hexane/ethyl acetate=9/1) to give 2-(4-(3-methoxypropoxy) phenyl)-4,4,5,5-tetramethyl-1,3,2-dioxaborolane as a white solid (287.3 mg, 73%).

(2) Under a nitrogen atmosphere, 5-bromopyrazin-2-amine (54.0 mg, 0.3 mmol, 1 eq.) and 2-(4-(3-methoxypropoxy)phenyl)-4,4,5,5-tetramethyl-1,3,2-dioxaborolane obtained in (1) above (90.0 mg, 0.6 mmol, 1 eq.) were dissolved in ethanol (1 ml) and toluene (8 ml), to which 1 M aqueous sodium carbonate (3 ml) was then added and stirred at room temperature. The reaction mixture was degassed in vacuo, and a catalytic amount of tetrakistriphenylphosphine palladium (0) (in an amount of about one microspatula) was added thereto, followed by degassing again in vacuo and stirring overnight (12 hours) at 100° C. After cooling to room temperature, the palladium catalyst was removed by celite filtration. The resulting residue was extracted with ethyl acetate, washed with distilled water and saturated aqueous sodium chloride, dried over sodium sulfate, and then concentrated under reduced pressure. The resulting residue was purified by column chromatography (eluent: hexane/ethyl acetate=7/3->1/1) to give 5-(4-(3-methoxypropoxy)phenyl)pyrazin-2-amine as a yellow solid (80 mg, 100%).

$^{1}$H-NMR (500 MHz, $CDCl_3$): δ (ppm)=7.73 (d, J=8.5 Hz, 2H), 6.89 (d, J=8.5 Hz, 2H), 4.05 (t, J=5.1 Hz, 2H), 3.97 (t, J=5.4 Hz, 2H), 1.33 (m, 12H), 0.90 (s, 9H), 0.09 (s, 6H). $^{13}$C-NMR (150 MHz, $CDCl_3$): δ (ppm)=−5.05, 18.54, 24.99, 26.05, 62.07, 69.18, 83.66, 114.02, 136.61, 161.64.

(3) Under an argon atmosphere, 5-(4-(3-methoxypropoxy)phenyl)pyrazin-2-amine obtained in (2) above (30.0 mg, 0.08 mmol, 1 eq.) and 1,1-diethoxy-3-phenylpropan-2-one (38.0 mg, 0.17 mmol, 2 eq.) were dissolved in ethanol (2 ml) and milliQ water (0.2 ml), and then cooled to 0° C. The reaction mixture was degassed in vacuo, and concentrated hydrochloric acid (0.1 ml) was added thereto, followed by stirring overnight (16 hours) at 80° C. After cooling to room temperature, the reaction mixture was concentrated under reduced pressure, and the residue was purified by silica column chromatography (methylene chloride/methanol=20/1) to give 2-benzyl-6-(4-(3-methoxypropoxy)phenyl)imidazo[1,2-a]pyrazin-3(7H)-one as a yellow solid (22.6 mg, 55%).

$^1$H-NMR (500 MHz, $CD_3OD$): δ (ppm)=7.88 (s, 1H), 7.63 (s, 1H), 7.55 (d, J=8.5 Hz, 2H), 7.28-7.11 (m, 5H), 7.00 (d, J=8.6 Hz, 2H), 4.09 (s, 2H), 4.06 (t, J=6.2 Hz, 2H), 3.53 (t, J=6.1 Hz, 2H), 3.26 (q, J=3.2 Hz, 3H). $^{13}$C-NMR (125 MHz, $CD_3OD$): δ (ppm)=161.75, 139.52, 129.94, 129.53, 128.74, 127.48, 116.23, 108.44, 70.17, 66.10, 58.91, 34.43, 30.52.

Example 2

Synthesis of 6-(4-(3-methoxypropoxy)phenyl)-2-methylimidazo[1,2-a]pyrazin-3(7H)-one (HuLumino22)

[Formula 29]

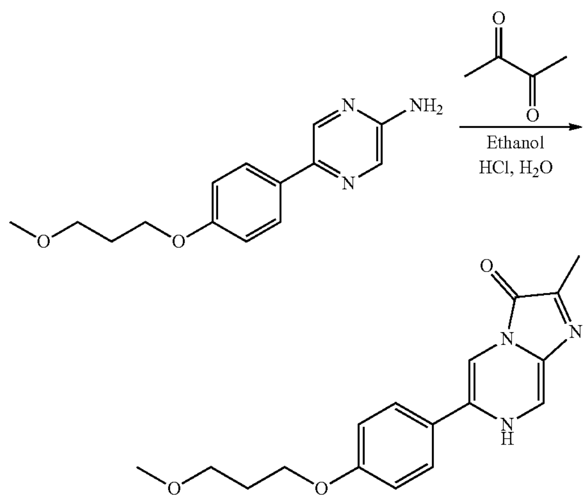

<Synthesis Method>

Under an argon atmosphere, 5-(4-(3-methoxypropoxy)phenyl)pyrazin-2-amine (30.0 mg, 0.11 mmol, 1 eq.) and diacetyl (19.9 mg, 0.23 mmol, 2 eq.) were dissolved in ethanol (2 ml) and milliQ water (0.2 ml), and then cooled to 0° C. The reaction mixture was degassed in vacuo, and concentrated hydrochloric acid (0.1 ml) was added thereto, followed by stirring overnight (16 hours) at 80° C. After cooling to room temperature, the reaction mixture was concentrated under reduced pressure, and the residue was purified by silica column chromatography (methylene chloride/methanol=20/1) to give 6-(4-(3-methoxypropoxy)phenyl)-2-methylimidazo[1,2-a]pyrazin-3(7H)-one as a yellow solid (22.6 mg, 10%).

$^1$H-NMR (500 MHz, $CD_3OD$): δ (ppm)=7.88 (s, 1H), 7.60 (d, J=8.7 Hz, 2H), 7.06 (d, J=8.7 Hz, 2H), 4.12 (t, J=6.2 Hz, 2H), 3.58 (t, J=6.2 Hz, 2H), 3.35 (s, 3H), 2.05 (t, J=12.4 Hz, 2H).

Example 3

Synthesis of (E)-2-benzyl-6-(4-(trifluoromethyl)styryl)imidazo[1,2-a]pyrazin-3(7H)-one (HuLumino32)

[Formula 30]

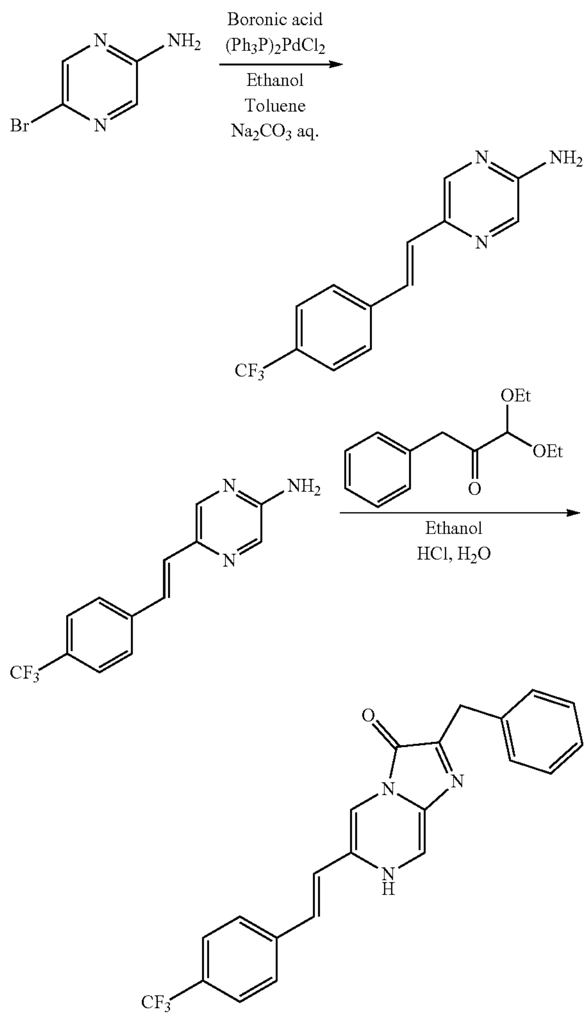

<Synthesis Method>

(1) Under a nitrogen atmosphere, 5-bromopyrazin-2-amine (100.0 mg, 0.57 mmol, 1 eq.) and (E)-(4-(trifluoromethyl)styryl) boronic acid (196 mg, 0.91 mmol, 1.6 eq.) were dissolved in ethanol (1.6 ml) and toluene (10 ml), to which 1 M aqueous sodium carbonate (4 ml) was then added and stirred at room temperature. The reaction mixture was degassed in vacuo, and a catalytic amount of tetrakistriphenylphosphine palladium (0) (in an amount of about one microspatula) was added thereto, followed by degassing again in vacuo and stirring overnight (12 hours) at 100° C. After cooling to room temperature, the palladium catalyst was removed by celite filtration. The resulting residue was extracted with ethyl acetate, washed with distilled water and saturated aqueous sodium chloride, dried over sodium sulfate, and then concentrated under reduced pressure. The resulting residue was purified by column chromatography (eluent: hexane/ethyl acetate=1/1) to give (E)-5-(4-(trifluoromethyl)styryl)pyrazin-2-amine as a yellow solid (144.4 mg, 95%).

$^{1}$H-NMR (500 MHz, $CDCl_3$): δ (ppm)=8.07 (d, J=1.1 Hz, 2H), 8.02 (d, J=1.2 Hz, 2H), 7.60 (q, J=1.8 Hz, 4H), 7.46 (d, J=16.0 Hz, 1H), 7.12 (d, J=16.0 Hz, 1H), 4.73 (s, 2H). $^{13}$C-NMR (125 MHz, $CDCl_3$): δ (ppm)=153.43, 141.61, 140.78, 140.58, 132.42, 129.66, 129.40, 128.10, 126.88, 125.79, 125.76.

(2) Under an argon atmosphere, (E)-5-(4-(trifluoromethyl)styryl)pyrazin-2-amine obtained in (1) above (30.0 mg, 0.05 mmol, 1 eq.) and 1,1-diethoxy-3-phenylpropan-2-one (30.1 mg, 0.13 mmol, 2 eq.) were dissolved in ethanol (2 ml) and milliQ water (0.2 ml), and then cooled to 0° C. The reaction mixture was degassed in vacuo, and concentrated hydrochloric acid (0.1 ml) was added thereto, followed by stirring overnight (16 hours) at 80° C. After cooling to room temperature, the reaction mixture was concentrated under reduced pressure, and the residue was purified by silica column chromatography (methylene chloride/methanol=20/1) to give (E)-2-benzyl-6-(4-(trifluoromethyl)styryl)imidazo[1,2-a]pyrazin-3(7H)-one as a yellow solid (22.6 mg, 55%).

$^{1}$H-NMR (500 MHz, $CDCl_3$): δ (ppm)=7.76 (s, 1H), 7.70-7.61 (m, 6H), 7.34-7.29 (m, 3H), 7.21-7.16 (m, 2H), 7.06 (d, J=16.5 Hz, 1H), 4.40 (s, 2H).

Comparative Examples 1 to 4 and Comparative Examples 5 to 7

NCTZ (Native CTZ; FUJIFILM Wako Pure Chemical Corporation, Japan), DeepBlueC™ (NanoLight), MCLA™ (Cayman Chemical) and BBlue2.3 (see Non-patent Document 4: R. Nishihara et al., Theranostics, 2019, 9, 2646-2661.) represented by the structural formulae shown below were used as compounds according to Comparative Examples 1 to 4, in this order, respectively.

[Formula 31]

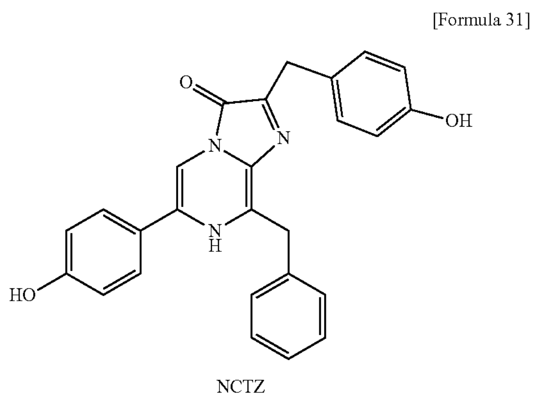

NCTZ

-continued

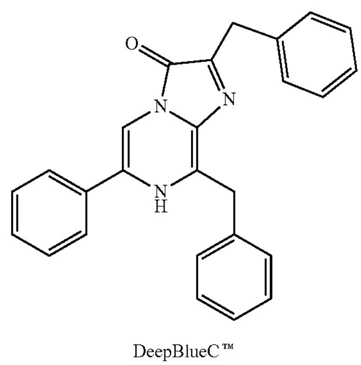

DeepBlueC™

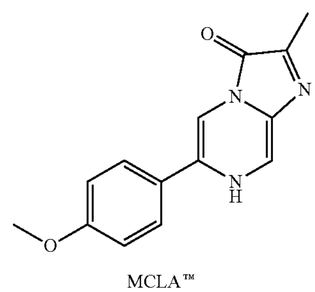

MCLA™

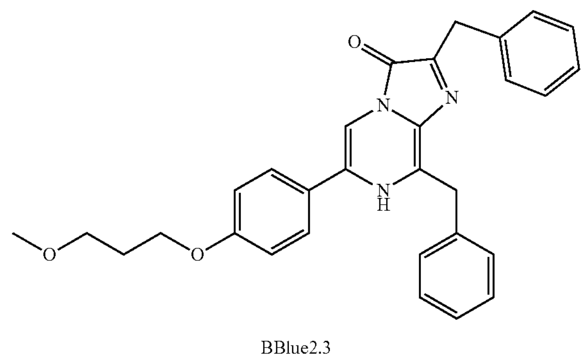

BBlue2.3

Likewise, control compounds 1 to 3 represented by the structural formulae shown below (for all, see Non-patent Document 3: T. Hirano et al., Tetrahedron Letters, 1992, 33, 5771-5774.) were used as compounds according to Comparative Examples 5 to 7, in this order, respectively.

[Formula 32]

Control Compound 1

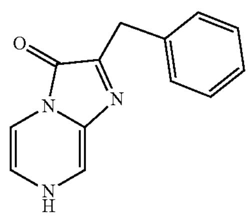

-continued

Control Compound 2

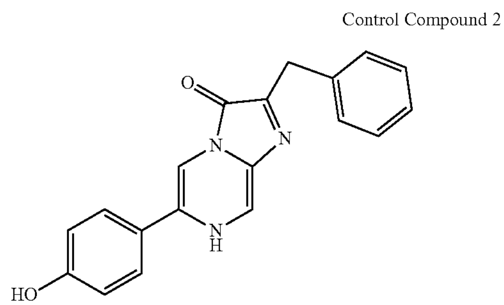

Control Compound 3

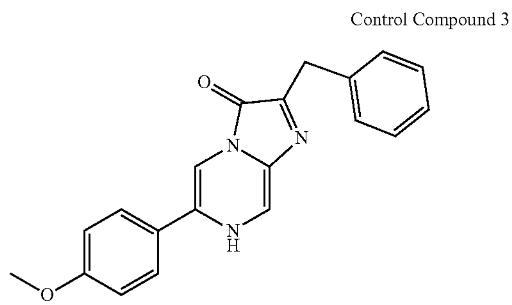

Example 4

Synthesis of (E)-2-benzyl-6-(4-methoxystyryl)imidazo[1,2-a]pyrazin-3(7H)-one (HuLumino30)

[Formula 33]

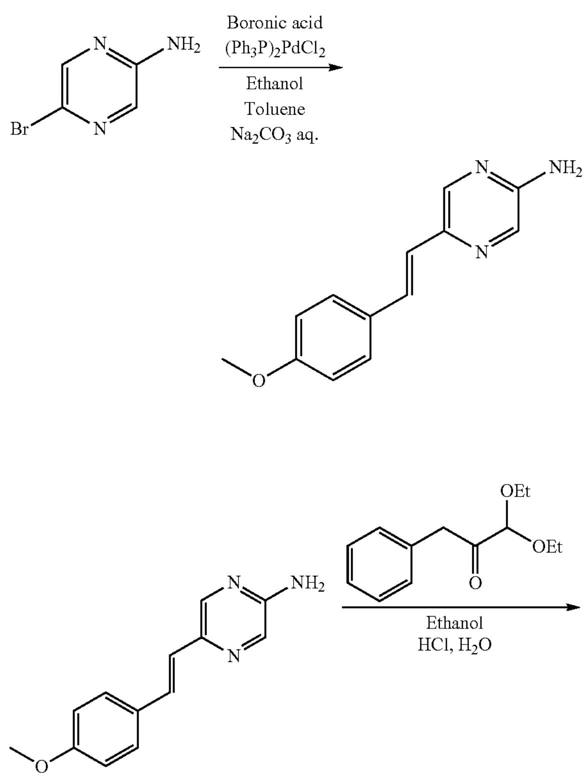

-continued

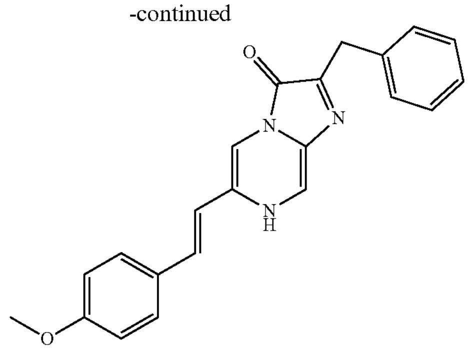

<Synthesis Method>

(1) Under an argon atmosphere, 5-bromopyrazin-2-amine (500.0 mg, 2.87 mmol, 1 eq.) and (E)-(4-methoxystyryl) boronic acid (818 mg, 4.34 mmol, 1.6 eq.) were dissolved in ethanol (4.8 ml) and toluene (30 ml), to which 1 M aqueous sodium carbonate (12 ml) was then added and stirred at room temperature. The reaction mixture was degassed in vacuo, and a catalytic amount of tetrakistriphenylphosphine palladium (0) (in an amount of about one microspatula) was added thereto, followed by degassing again in vacuo and stirring overnight at 100° C. After cooling to room temperature, the palladium catalyst was removed by celite filtration. The resulting residue was extracted with ethyl acetate, washed with distilled water and saturated aqueous sodium chloride, dried over sodium sulfate, and then concentrated under reduced pressure. The resulting residue was purified by column chromatography (eluent: hexane/ethyl acetate=1/1) to give (E)-5-(4-methoxystyryl)pyrazin-2-amine as a yellow solid (423.0 mg, 64%).

$^1$H-NMR (500 MHz, CDCl3): δ (ppm)=8.04 (s, 1H), 7.98 (s, 1H), 7.47 (d, J=8.6 Hz, 2H), 7.39 (d, J=16.0 Hz, 1H), 6.93 (d, 1H), 6.89 (d, J=8.8 Hz, 2H), 4.61 (s, 2H), 3.82 (s, 3H). $^{13}$C-NMR (125 MHz, $CDCl_3$): δ (ppm)=159.53, 152.71, 141.89, 140.61, 131.98, 129.77, 129.34, 128.00, 122.19, 114.17, 55.33.

(2) Under an argon atmosphere, (E)-4-(2-(5-aminopyrazin-2-yl)vinyl) phenol (30.0 mg, 0.14 mmol, 1 eq.) and 1,1-diethoxy-3-phenylpropan-2-one (37.3 mg, 0.16 mmol, 1.2 eq.) were dissolved in ethanol (2 ml) and milliQ water (0.2 ml), and then cooled to 0° C. The reaction mixture was degassed in vacuo, and concentrated hydrochloric acid (0.1 ml) was added thereto, followed by stirring overnight at 80° C. After cooling to room temperature, the reaction mixture was concentrated under reduced pressure, and the residue was purified by silica column chromatography (methylene chloride/methanol=10/1) to give (E)-2-benzyl-6-(4-methoxystyryl)imidazo[1,2-a]pyrazin-3(7H)-one as a yellow solid (10.3 mg, 21%).

$^1$H-NMR (500 MHz, CD3OD, CDCl3): δ (ppm)=7.70 (s, 1H), 7.65 (s, 1H), 7.50-7.17 (m, 7H), 7.07 (d, J=16.5 Hz, 1H), 6.93 (d, J=8.7 Hz, 2H), 6.76 (d, J=16.4 Hz, 1H), 4.15 (s, 2H), 3.84 (s, 3H).

Example 5

Synthesis of (E)-6-(2-([1,1'-biphenyl]-4-yl)vinyl)-2-benzylimidazo[1,2-a]pyrazin-3(7H)-one (HuLumino44)

[Formula 34]

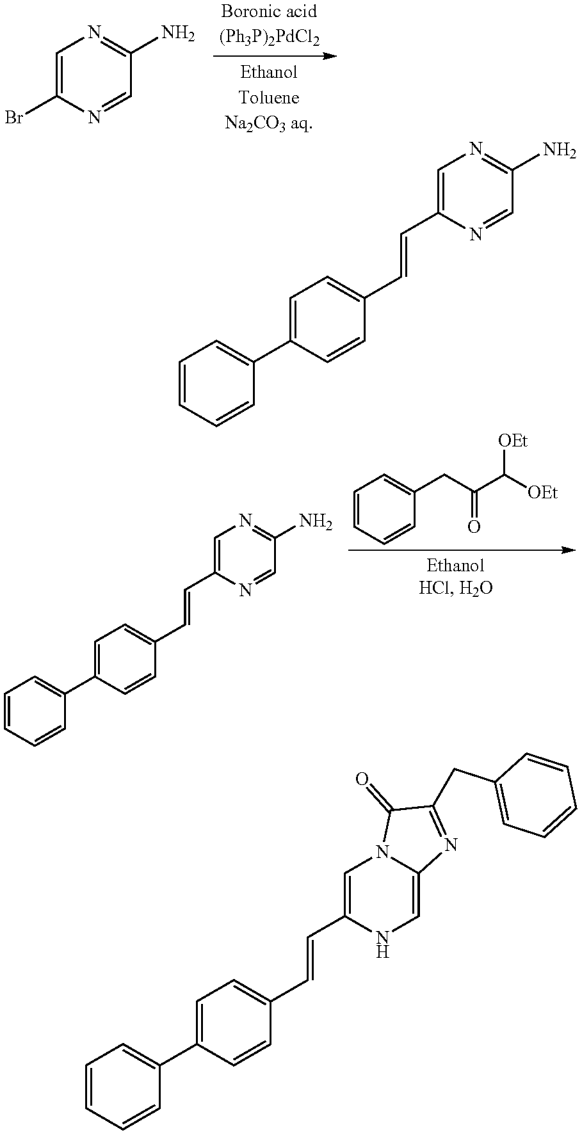

<Synthesis Method>

(1) Under an argon atmosphere, 5-bromopyrazin-2-amine (150.0 mg, 0.86 mmol, 1 eq.) and (E)-(2-([1,1'-biphenyl]-4-yl)vinyl) boronic acid (309 mg, 1.37 mmol, 1.6 eq.) were dissolved in ethanol (4 ml) and toluene (20 ml), to which 1 M aqueous sodium carbonate (8 ml) was then added and stirred at room temperature. The reaction mixture was degassed in vacuo, and a catalytic amount of tetrakistriphenylphosphine palladium (0) (in an amount of about one microspatula) was added thereto, followed by degassing again in vacuo and stirring overnight at 100° C. After cooling to room temperature, the palladium catalyst was removed by celite filtration. The resulting residue was extracted with ethyl acetate, washed with distilled water and saturated aqueous sodium chloride, dried over sodium sulfate, and then concentrated under reduced pressure. The resulting residue was purified by column chromatography (eluent: hexane/ethyl acetate=1/2) to give (E)-5-(2-([1,1'-biphenyl]-4-yl)vinyl)pyrazin-2-amine as a yellow solid (114.0 mg, 48%).

$^1$H-NMR (500 MHz, $CDCl_3$): δ (ppm)=8.08 (s, 1H), 8.02 (s, 1H), 7.62-7.33 (m, 11H), 7.10 (d, J=16.0 Hz, 1H), 4.63 (s, 2H). $^{13}$C-NMR (125 MHz, $CDCl_3$): δ (ppm)=152.92, 141.53, 141.03, 140.65, 140.60, 136.03, 132.12, 129.24, 128.81, 127.38, 127.17, 126.93, 124.29.

(2) Under an argon atmosphere, (E)-5-(2-([1,1'-biphenyl]-4-yl)vinyl)pyrazin-2-amine (31.7 mg, 0.11 mmol, 1 eq.) and 1,1-diethoxy-3-phenylpropan-2-one (30.6 mg, 0.13 mmol, 1.2 eq.) were dissolved in ethanol (2 ml) and milliQ water (0.2 ml), and then cooled to 0° C. The reaction mixture was degassed in vacuo, and concentrated hydrochloric acid (0.1 ml) was added thereto, followed by stirring for 6 hours at 80° C. After cooling to room temperature, the reaction mixture was concentrated under reduced pressure, and the residue was purified by silica column chromatography (methylene chloride/methanol=10/1) to give (E)-6-(2-([1,1'-biphenyl]-4-yl)vinyl)-2-benzylimidazo[1,2-a]pyrazin-3(7H)-one as a yellow solid (6.4 mg, 13%).

$^1$H-NMR (500 MHz, CDCl3, CD3OD): δ (ppm)=7.73-7.00 (m, 18H), 4.37 (s, 2H).

Example 6

Synthesis of (E)-2-benzyl-6-styrylimidazo[1,2-a]pyrazin-3(7H)-one (HuLumino45)

[Formula 35]

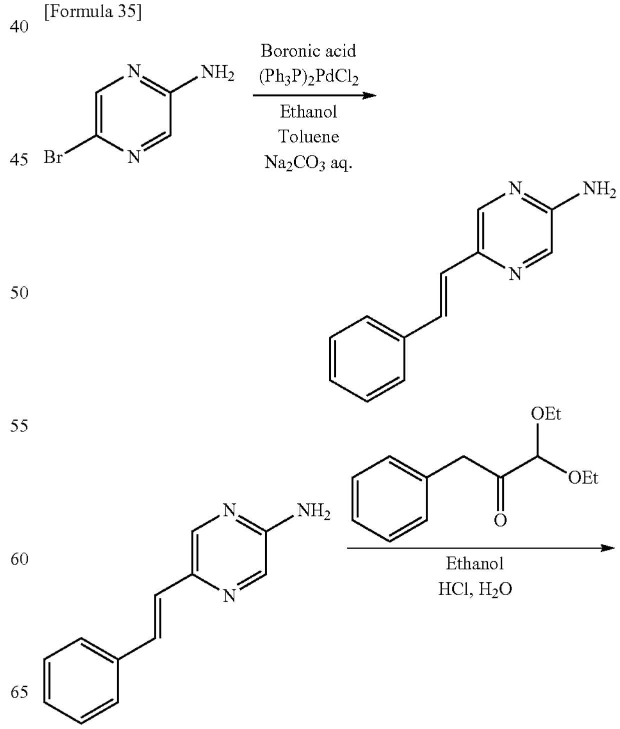

-continued

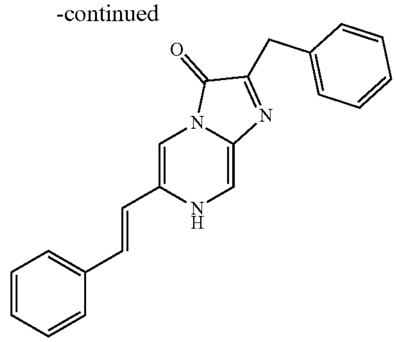

<Synthesis Method>

(1) Under an argon atmosphere, 5-bromopyrazin-2-amine (150.0 mg, 0.86 mmol, 1 eq.) and (E)-styrylboronic acid (204 mg, 1.37 mmol, 1.6 eq.) were dissolved in ethanol (4 ml) and toluene (20 ml), to which 1 M aqueous sodium carbonate (8 ml) was then added and stirred at room temperature. The reaction mixture was degassed in vacuo, and a catalytic amount of tetrakistriphenylphosphine palladium (0) (in an amount of about one microspatula) was added thereto, followed by degassing again in vacuo and stirring overnight at 100° C. After cooling to room temperature, the palladium catalyst was removed by celite filtration. The resulting residue was extracted with ethyl acetate, washed with distilled water and saturated aqueous sodium chloride, dried over sodium sulfate, and then concentrated under reduced pressure. The resulting residue was purified by column chromatography (eluent: hexane/ethyl acetate=1/2) to give (E)-5-styrylpyrazin-2-amine as a yellow solid (153.6 mg, 90%).

$^1$H-NMR (500 MHz, CDCl3): δ (ppm)=8.06 (s, 1H), 8.00 (s, 1H), 7.54-7.25 (m, 6H), 7.05 (d, J=16.0 Hz, 1H), 4.67 (s, 2H). $^{13}$C-NMR (125 MHz, $CDCl_3$): δ (ppm)=153.09, 141.57, 141.08, 137.07, 132.21, 129.82, 128.82, 128.00, 126.84, 124.39.

(2) Under an argon atmosphere, (E)-5-styrylpyrazin-2-amine (30.0 mg, 0.15 mmol, 1 eq.) and 1,1-diethoxy-3-phenylpropan-2-one (40.6 mg, 0.18 mmol, 1.2 eq.) were dissolved in ethanol (2 ml) and milliQ water (0.2 ml), and then cooled to 0° C. The reaction mixture was degassed in vacuo, and concentrated hydrochloric acid (0.1 ml) was added thereto, followed by stirring overnight at 80° C. After cooling to room temperature, the reaction mixture was concentrated under reduced pressure, and the residue was purified by silica column chromatography (methylene chloride/methanol=10/1) to give (E)-2-benzyl-6-styrylimidazo [1,2-a]pyrazin-3(7H)-one as a yellow solid (6.0 mg, 12%).

$^1$H-NMR (500 MHz, CDCl3, CD3OD): δ (ppm)=7.76-6.92 (m, 14H), 4.44 (s, 2H).

Method for Luminescence Activity Measurement and the Results of Luminescence Intensity Comparison Human serum albumin (human serum-derived lyophilized powder, Fatty acid free, Globulin free, Sigma-Aldrich), other human protein species or bovine serum albumin (bovine serum-derived lyophilized powder, Sigma-Aldrich) was dissolved in PB Buffer (10 mM, pH 7.4) and used directly for luminescence measurement. As luminescent substrates, NCTZ, DeepBlueC™, MCLA™, control compounds 1 to 3, HuLumino12 and HuLumino22 were used. Each luminescent substrate was dissolved in methanol to give a 2 mM solution. This solution was diluted to 10 UM with 10 mM PB buffer (pH 7.4) for use as a substrate solution. To 90 μL of this solution, 10 μL of 10 mM PB buffer (pH 7.4) containing human serum albumin (HSA) or bovine serum albumin (BSA) was added to initiate a luminescent reaction. The luminescence intensity was measured with a Promega GloMax® 20/20 for 60 seconds, and the results were expressed as total luminescence (Total Luminescence/min) and compared (FIG. 1). Moreover, Table A below shows the results of luminescence intensity comparison normalized against the luminescence intensity of native coelenterazine in HSA which was set to 1.0.

TABLE 7

Table A: Luminescence intensity comparison

| Example | | BSA Luminescence intensity | HSA Luminescence intensity |
|---|---|---|---|
| Comparative Example 1 | NCTZ | 3.9 | 1.0 |
| Comparative Example 2 | DeepBlueC ™ | 7.6 | 22.1 |
| Comparative Example 3 | MCLA ™ | 1.8 | 14.1 |
| Comparative Example 4 | BBlue2.3 | 34.3 | 51.5 |
| Comparative Example 5 | Control compound 1 | N.D. | N.D. |
| Comparative Example 6 | Control compound 2 | 11.2 | 13.7 |
| Comparative Example 7 | Control compound 3 | 34.4 | 554 |
| Example 1 | HuLumino12 | 11.9 | 912 |
| Example 2 | HuLumino22 | 3.1 | 14.2 |
| Example 3 | HuLumino32 | 778.4 | 1106 |
| Example 4 | HuLumino30 | 19.2 | 154 |
| Example 5 | HuLumino44 | 5.2 | 206 |
| Example 6 | HuLumino45 | 9.8 | 61.3 |

N.D.: not detectable due to low luminescence brightness

As can be seen from FIG. 1 and Table A, the novel compounds of the present invention show significant luminescence when recognized by human serum albumin (HSA). In particular, the combination of HuLumino12/HSA was found to show 912-fold higher luminescence intensity than NCTZ/HSA. In addition, the Michaelis-Menten constant is 4.2 μM and 25.3 μM in HuLumino12/HSA and NCTZ/HSA, respectively, thus indicating that the luminescent molecules of the present invention show higher affinity with HSA than conventional molecules. Moreover, HuLumino32 with a relatively high fluorescence quantum yield was found to show the highest luminescence intensity in both BSA and HSA.

Figure 2:
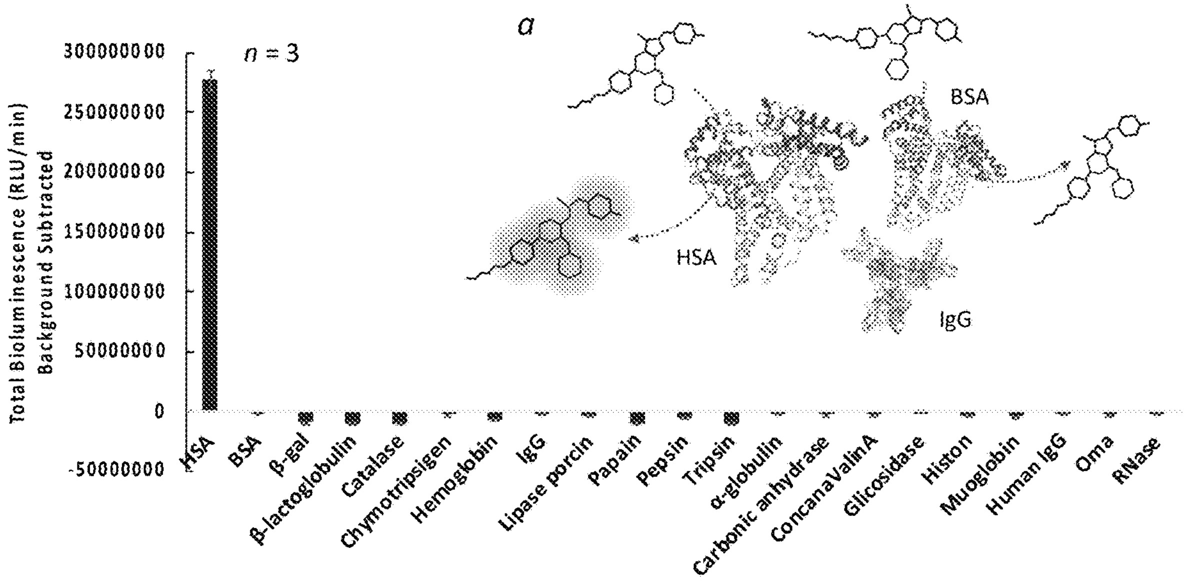
FIG. 2 is a graph showing the luminescence intensity of HuLumino12 (a compound according to an example of the present invention) upon reaction with various human-derived proteins or bovine serum albumin. In the figure, inset a shows a schematic diagram.

As can be seen from FIG. 2, the novel compound HuLumino12 of the present invention was found to show a specific luminescent reaction when recognized by human serum albumin (HSA) among various human protein species.

Figure 3:
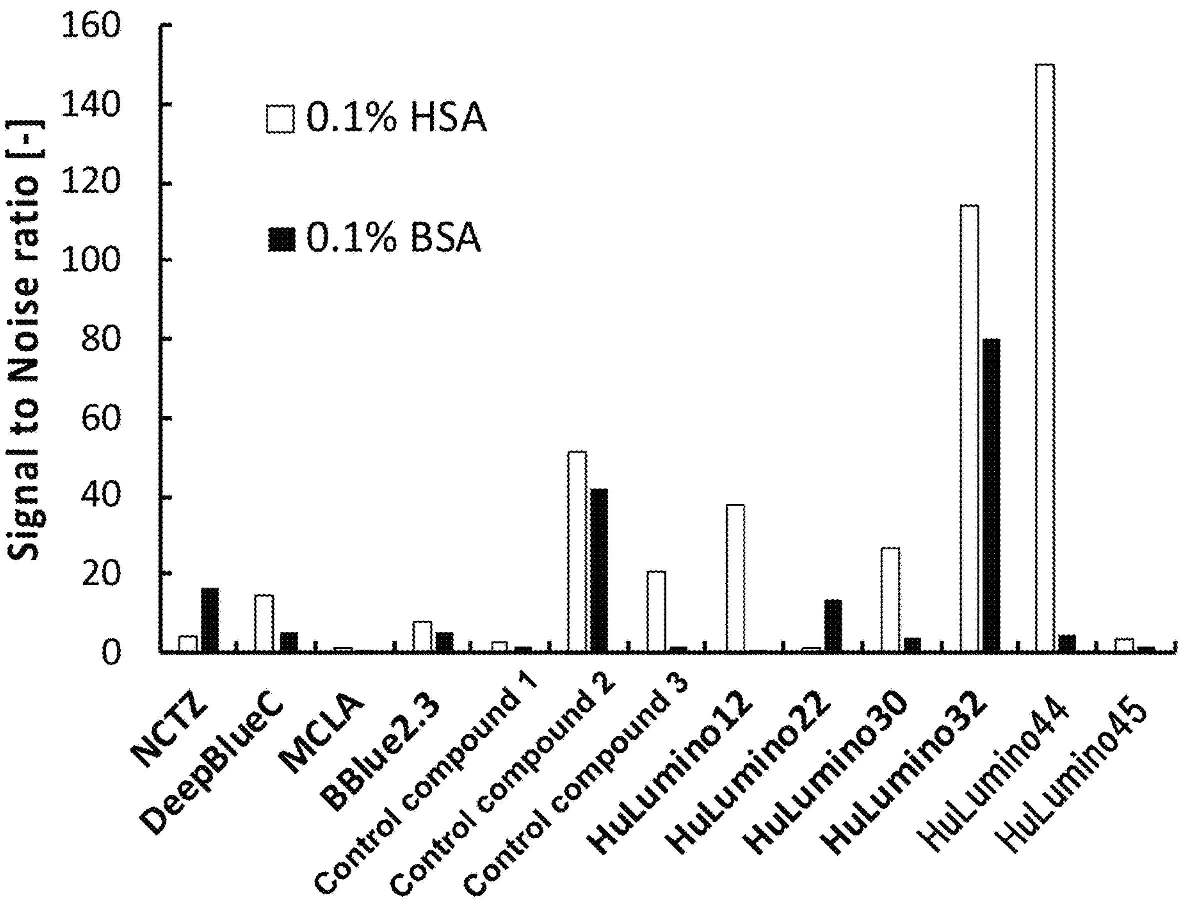
FIG. 3 is a graph showing the luminescence property (signal to noise ratio, S/N ratio) of compounds according to examples of the present invention and comparative examples in the presence of human serum albumin (HSA).
Figure 4:
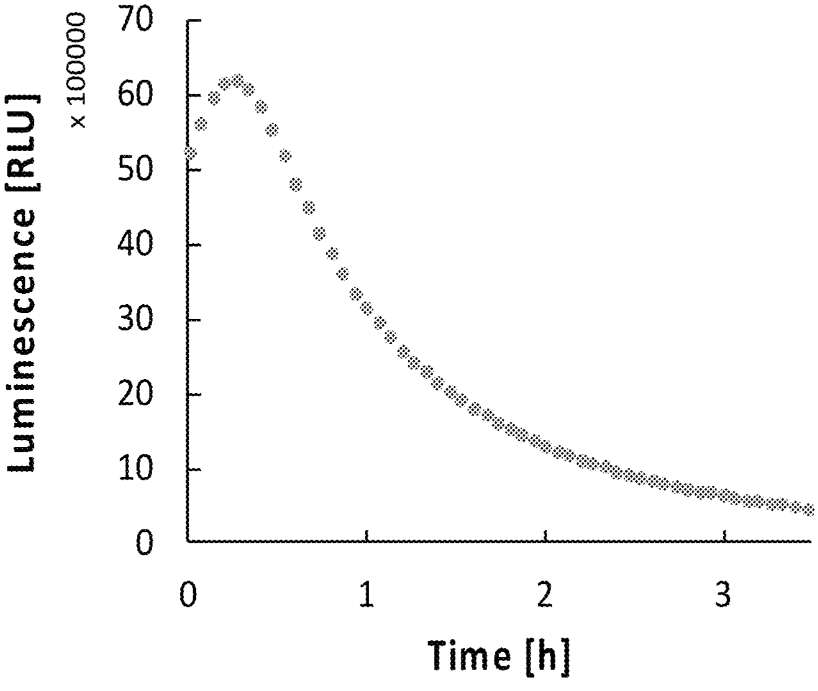
FIG. 4 is a graph showing the luminescence property (luminescence duration) of HuLumino12 (a compound according to an example of the present invention) in the presence of human serum albumin (HSA).

As can be seen from FIG. 3, the S/N ratio was 37 in the luminescent reaction between the novel compound HuLumino12 of the present invention and HSA, while the luminescence duration in this reaction was found to reach 3 hours, as shown in FIG. 4. Moreover, as can be seen from FIG. 3, the S/N ratio was 150 in the luminescent reaction between the novel compound HuLumino44 of the present invention and HSA, thus indicating that HuLumino44 resulted in an approximately 4-fold higher S/N ratio than that of HuLumino12 and was excellent in optical properties.

Figure 5:
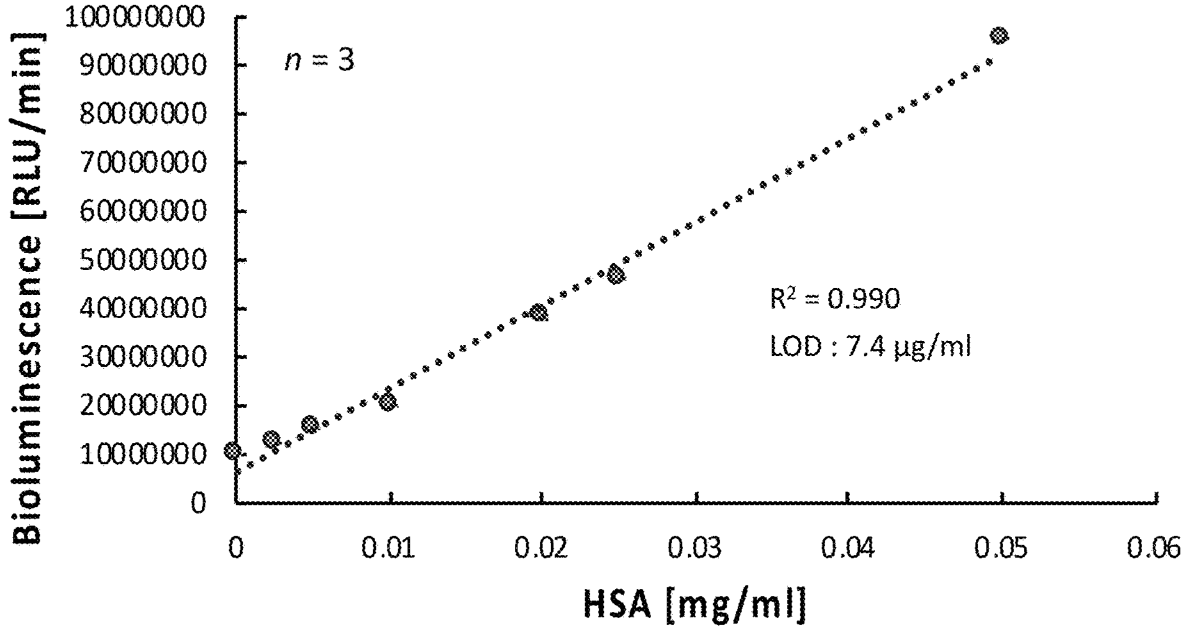
FIG. 5 is a graph showing the luminescence intensity of HuLumino12 (a compound according to an example of the present invention), which is dependent on the concentration of human serum albumin (HSA).

As can be seen from FIG. 5, the detection limit of HSA detection with the novel compound HuLumino12 of the present invention was found to be 7.4 μg/mL.

Method for Luminescence Spectrum Measurement

Figure 6:
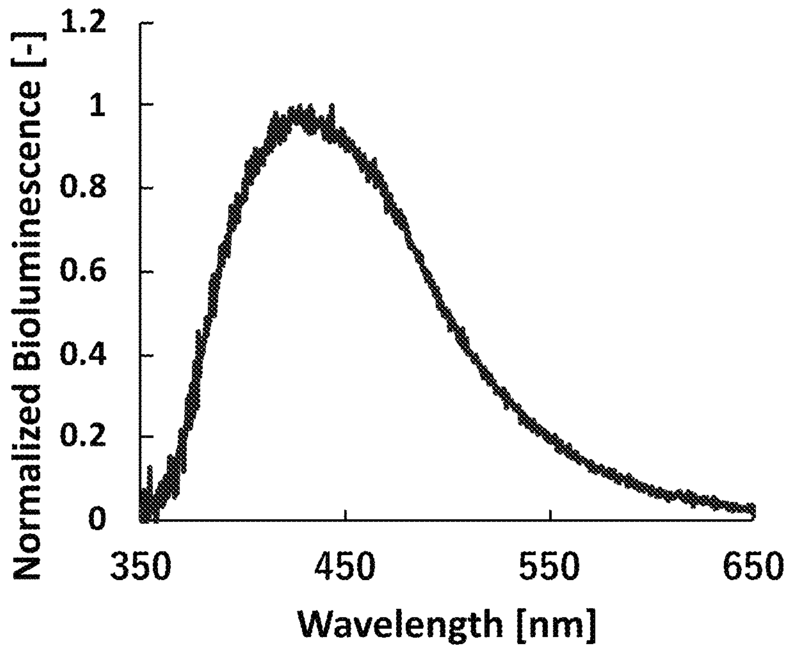
FIG. 6 is a graph showing the luminescence wavelength (luminescence spectrum measurement result) of HuLumino12 (a compound according to an example of the present invention) in the presence of human serum albumin (HSA).

Luminescence spectrum measurement was performed in the same manner as used in the above luminescence intensity measurement, thus indicating that the peak luminescence wavelength was 427 nm (FIG. 6). The luminescence spectrum was measured with a spectrometer. The peak luminescence wavelength was obtained by being normalized against the peak luminescence intensity which was set to 1.0.

The design of the CTZ derivatives obtained in the present invention may also be applied to other bioluminescent systems. *Oplophorus gracilirostris* uses CTZ as a luminescent substrate. *Oplophorus gracilirostris*-derived luciferase NanoLuc (trade name) (Promega) (reference document: Hall P. M. et al., *ACS. Chem. Biol.,* 2012, 7, 1848-1857.) has been developed in recent years and, when combined with its substrate furimazine, has about 100-fold higher luminescence intensity than the firefly luciferase luminescent system. This luciferase has been demonstrated for its application not only to reporter assays, but also to various bioassay systems including protein-protein interaction analysis based on the bioluminescence resonance energy transfer (BRET) mechanism (reference document: England G. C. et al., *Bioconjugate Chem.,* 2016, 27, 1175-1187).

In substrate synthesis studies for NanoLuc (trade name) (Promega), CTZ derivatives modified at the 6- and 2-positions have been reported (reference document: Hall P. M. et al., *ACS. Chem. Biol.,* 2012, 7, 1848-1857; Shakhmin A. et al., *Chem. Eur. J.,* 2016, 22, 10369-10375), but these derivatives have been examined predominantly for the influence of their substituent at the 2-position on enzyme activity. According to the present invention, substituent modifications at the 6- and 8-positions of CTZ greatly affect enzyme activity; and hence further enhancement in the luminescence intensity of NanoLuc (trade name) (Promega) can be expected by the development of novel substrates with modifications at the 6- and 8-positions of CTZ.

INDUSTRIAL APPLICABILITY

The compound of the present invention can be used for detection of human-derived proteins, and also used as a reagent for luminescence detection of structural deterioration and aggregation of antibody proteins. This can be used for the quality control of antibody drugs and immunochromatographic in vitro diagnostic reagents. Moreover, binding between serum protein and drug can be rapidly determined by performing a competitive inhibition test with the compound of the present invention serving as a luminescent molecule. Thus, the compound of the present invention is helpful as one of the pharmacokinetic evaluation methods in the acceleration of drug design studies.

The invention claimed is:

1. A compound represented by the following formula [I], or a salt thereof, or a hydrate or solvate thereof:

[I]

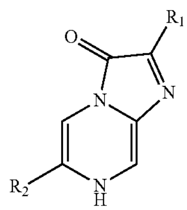

in formula [I], $R_1$ is —$CH_2$-A where A is a hydrogen atom or a group represented by the following formula:

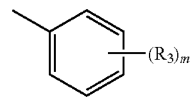

wherein $R_3$ is a hydrogen atom, a hydroxyl group, a fluorine atom, an alkyl group containing 1 to 5 carbon atoms, a methoxy group, or a trifluoromethyl group, and m is an integer of 1 to 5, or a group represented by the following formula:

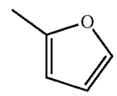

and $R_2$ is a group represented by the following formula:

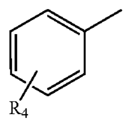

wherein $R_4$ is (i) —O—$(CH_2)_n$—$R_6$ (where $R_6$ is a hydroxyl group, a methoxy group, a methyl group, a trifluoromethyl group or an azido group, and n is an integer of 1 to 5, (ii) an alkyl group containing 1 to 5 carbon atoms, or (iii) any one of the groups represented by the following formulae:

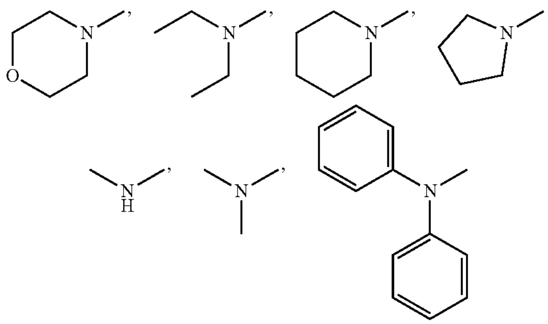

or a group represented by the following formula:

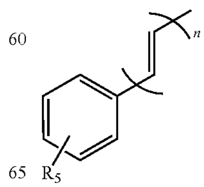

wherein any of the following (i) to (iv) apply:

(i) $R_5$ is a hydrogen atom, a hydroxyl group, a methoxy group, a methyl group, a trifluoromethyl group, a dimethylamino group, a phenyl group, or an azido group, and n is an integer of 1 to 5, (ii) $R_5$ is an alkyl group containing 1 to 5 carbon atoms, and n is an integer of 1 to 5, (iii) $R_5$ is $—O—(CH_2)_p—R_7$ where $R_7$ is a hydroxyl group, a methoxy group, a methyl group, a trifluoromethyl group, a dimethylamino group, an azido group, or an alkyl group containing 1 to 5 carbon atoms, and p is an integer of 1 to 5, and n is an integer of 1 to 5, or (iv) $R_5$ is any one of the groups represented by the following formulae:

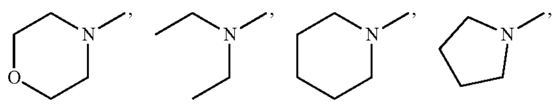

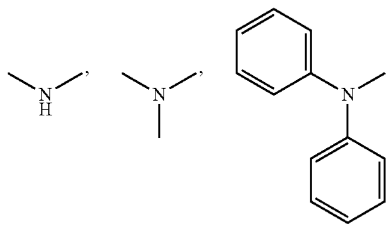

and n is an integer of 1 to 5;

provided that the A is not a hydrogen when the $R_2$ is the group represented by the following formula

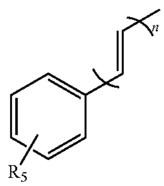

and provided that when m is 1 and $R_3$ is a hydroxyl group, $R_4$ is not

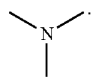

2. The compound according to claim 1, or a salt thereof, or a hydrate or solvate thereof, wherein the compound represented by formula [I] is a compound represented by the following formula [II]:

(II)

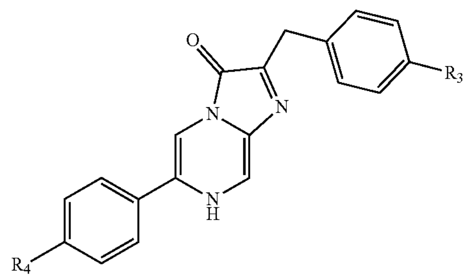

in formula [II], $R_3$ is a hydrogen atom, a hydroxyl group, a fluorine atom, an alkyl group containing 1 to 5 carbon atoms, a methoxy group, or a trifluoromethyl group, and $R_4$ is (i) $—O—(CH_2)_n—R_6$ where $R_6$ is a hydroxyl group, a methoxy group, a methyl group, a trifluoromethyl group or an azido group, and n is an integer of 1 to 5, (ii) an alkyl group containing 1 to 5 carbon atoms, or (iii) a group represented by any one of the following formulae:

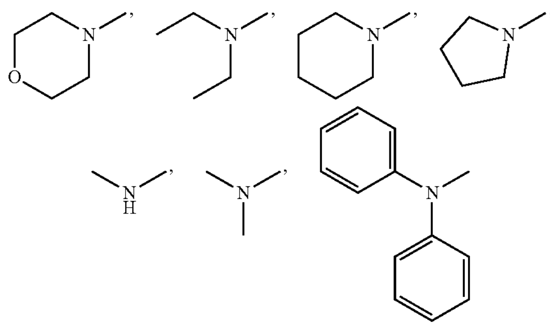

and provided that when $R_3$ is a hydroxyl group, $R_4$ is not

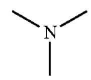

3. The compound according to claim 1, or a salt thereof, or a hydrate or solvate thereof, wherein $R_3$ and $R_4$ in formula [I] are, in combination, selected from the combinations of groups or atoms indicated in the table below:

TABLE 1

| $R_3$ | $R_4$ |
|---|---|
| —OH | $—O—(CH_2)_2—OH$ |
| —OH | $—O—(CH_2)_3—OH$ |
| —OH | $—O—(CH_2)_4—OH$ |
| —OH | $—O—(CH_2)_5—OH$ |
| —OH | $—O—(CH_2)_3—OCH_3$ |
| —OH | $—O—(CH_2)_2—N_3$ |
| —OH | $—O—(CH_2)_3—CH_3$ |
| —H | $—O—(CH_2)_2—OH$ |
| —H | $—O—(CH_2)_3—OH$ |
| —H | $—O—(CH_2)_4—OH$ |
| —H | $—O—(CH_2)_5—OH$ |

TABLE 1-continued

| $R_3$ | $R_4$ |
|---|---|
| —H | —O—$(CH_2)_3$—$OCH_3$ |
| —H | —O—$(CH_2)_3$—$CH_3$ |
| —OH | —$C_2H_5$ |
| —H | —$C_2H_5$ |
| —OH | —$CH_3$ |
| —H | —$CH_3$. |

4. The compound according to claim 3, or a salt thereof, or a hydrate or solvate thereof, wherein $R_3$ is —H, and $R_4$ is —O—$(CH_2)_3$—$OCH_3$.

5. The compound according to claim 3, or a salt thereof, or a hydrate or solvate thereof, wherein $R_3$ is —OH, and $R_4$ is —O—$(CH_2)_3$—$OCH_3$.

6. The compound according to claim 1, or a salt thereof, or a hydrate or solvate thereof, wherein the compound represented by formula [I] is a compound represented by the following formula [III]:

[III]

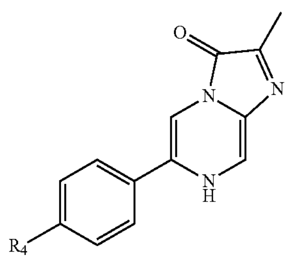

in formula [III], $R_4$ is (i) —O—$(CH_2)_n$—$R_6$ where $R_6$ is a hydroxyl group, a methoxy group, a methyl group, a trifluoromethyl group or an azido group, and n is an integer of 1 to 5, (ii) an alkyl group containing 1 to 5 carbon atoms, or (iii) a group represented by any one of the following formulae:

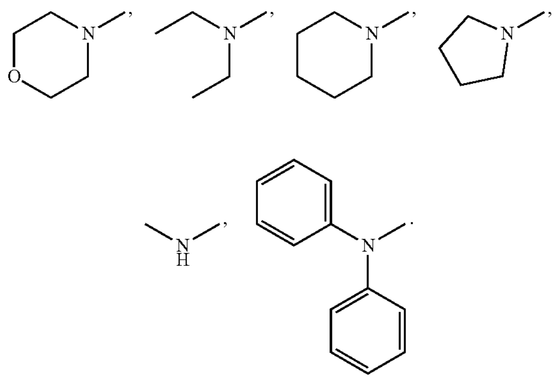

7. The compound according to claim 6, or a salt thereof, or a hydrate or solvate thereof, wherein $R_4$ in formula [III] is selected from the groups indicated in the table below:

TABLE 2

| $R_4$ |
|---|
| —O—$(CH_2)_2$—OH |
| —O—$(CH_2)_3$—OH |
| —O—$(CH_2)_4$—OH |
| —O—$(CH_2)_5$—OH |
| —O—$(CH_2)_3$—$OCH_3$ |
| —O—$(CH_2)_2$—$N_3$ |
| —O—$(CH_2)_3$—$CH_3$ |
| —$C_2H_5$ |
| —$CH_3$. |

8. The compound according to claim 7, or a salt thereof, or a hydrate or solvate thereof, wherein $R_4$ is —O—$(CH_2)_3$—$OCH_3$.

9. The compound according to claim 1, or a salt thereof, or a hydrate or solvate thereof, wherein the compound represented by formula [I] is a compound represented by the following formula [IV]:

[IV]

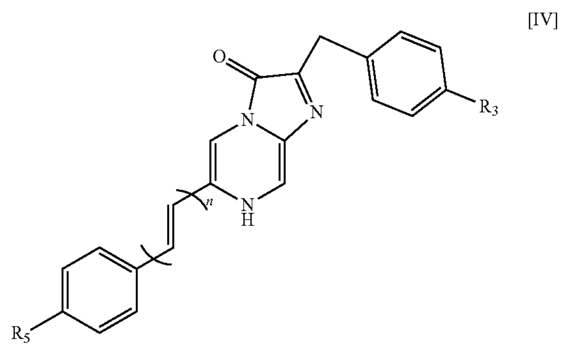

in formula [IV], $R_3$ is a hydrogen atom, a hydroxyl group, a fluorine atom, an alkyl group containing 1 to 5 carbon atoms, a methoxy group, or a trifluoromethyl group, and any of the following (i) to (iv) apply (i) $R_5$ is a hydrogen atom, a hydroxyl group, a methoxy group, a methyl group, a trifluoromethyl group, a dimethylamino group, a phenyl group, or an azido group, and n is an integer of 1 to 5, (ii) $R_5$ is an alkyl group containing 1 to 5 carbon atoms, and n is an integer of 1 to 5, (iii) $R_5$ is —O—$(CH_2)_p$—$R_7$ where $R_7$ is a hydroxyl group, a methoxy group, a methyl group, a trifluoromethyl group, a dimethylamino group, an azido group, or an alkyl group containing 1 to 5 carbon atoms, and p is an integer of 1 to 5, and n is an integer of 1 to 5, or (iv) $R_5$ is any one of the groups represented by the following formulae:

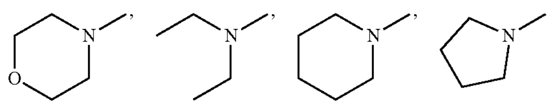

-continued

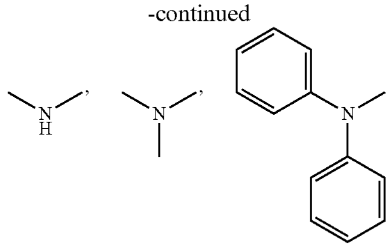

and n is an integer of 1 to 5.

10. The compound according to claim 9, or a salt thereof, or a hydrate or solvate thereof, wherein n and the groups or atoms represented by $R_3$ and $R_5$ in formula [IV] are, in combination, selected from the combinations indicated in the table below:

TABLE 3

| n | $R_3$ | $R_5$ |
|---|---|---|
| 1 | —OH | —OH |
| 1 | —H | —OH |
| 1 | —OH | —O—$CH_3$ |
| 1 | —H | —O—$CH_3$ |
| 1 | —OH | —$CF_3$ |
| 1 | —H | —$CF_3$ |
| 1 | —H | —N—$(CH_3)_2$ |
| 2 | —H | —O—$CH_3$ |
| 2 | —H | —OH |
| 2 | —H | —$CF_3$ |
| 2 | —H | —N—$(CH_3)_2$ |
| 3 | —H | —O—$CH_3$ |
| 3 | —H | —OH |
| 3 | —H | —$CF_3$ |
| 3 | —H | —N—$(CH_3)_2$ |
| 1 | —H | —O—$(CH_2)_2$—$N_3$ |
| 2 | —H | —O—$(CH_2)_3$—$OCH_3$ |
| 1 | —H | —$C_6H_5$ |
| 1 | —H | —H. |

11. The compound according to claim 10, or a salt thereof, or a hydrate or solvate thereof, wherein n is 1, $R_3$ is —H, and $R_5$ is —$OCH_3$.

12. The compound according to claim 10, or a salt thereof, or a hydrate or solvate thereof, wherein n is 1, $R_3$ is —H, and $R_5$ is —$CF_3$.

13. The compound according to claim 10, or a salt thereof, or a hydrate or solvate thereof, wherein n is 1, $R_3$ is —H, and $R_5$ is —$C_6H_5$.

14. The compound according to claim 10, or a salt thereof, or a hydrate or solvate thereof, wherein n is 1, $R_3$ is —H, and $R_5$ is —H.

15. A luminescent substrate for proteins or peptides, which comprises the compound according to claim 1, or a salt thereof, or a hydrate or solvate thereof.

16. A method for protein or peptide analysis, which comprises administering the compound according to claim 1, or a salt thereof, or a hydrate or solvate thereof, in vivo or adding the same in vitro to thereby detect a desired protein or peptide.

17. A method for protein or peptide analysis, which comprises administering the luminescent substrate according to claim 15 in vivo or adding the same in vitro to thereby detect a desired protein or peptide.

* * * * *